US009387245B2

(12) United States Patent
Johnson et al.

(10) Patent No.: US 9,387,245 B2
(45) Date of Patent: Jul. 12, 2016

(54) METHODS AND COMPOSITIONS FOR THE INHIBITION OF FRUCTOKINASE

(75) Inventors: Richard J. Johnson, Centennial, CO (US); Miguel A. Lanaspa-Garcia, Denver, CO (US); Takuji Ishimoto, Greenwood Village, CO (US)

(73) Assignee: University of Colorado, A Body Corporate, Denver, CO (US)

( * ) Notice: Subject to any disclaimer, the term of this patent is extended or adjusted under 35 U.S.C. 154(b) by 31 days.

(21) Appl. No.: 13/814,568

(22) PCT Filed: Aug. 8, 2011

(86) PCT No.: PCT/US2011/046938
§ 371 (c)(1),
(2), (4) Date: May 15, 2013

(87) PCT Pub. No.: WO2012/019188
PCT Pub. Date: Feb. 9, 2012

(65) Prior Publication Data
US 2013/0224218 A1 Aug. 29, 2013

Related U.S. Application Data

(60) Provisional application No. 61/371,255, filed on Aug. 6, 2010.

(51) Int. Cl.
| A61K 45/06 | (2006.01) |
| A61K 38/00 | (2006.01) |
| C12N 15/113 | (2010.01) |
| A61K 39/395 | (2006.01) |
| C07K 16/40 | (2006.01) |
| A61K 31/415 | (2006.01) |
| A61K 31/7052 | (2006.01) |
| A61K 31/427 | (2006.01) |
| C12N 9/12 | (2006.01) |
| A61K 31/425 | (2006.01) |

(52) U.S. Cl.
CPC ........... *A61K 39/3955* (2013.01); *A61K 31/415* (2013.01); *A61K 31/427* (2013.01); *A61K 31/7052* (2013.01); *A61K 38/005* (2013.01); *A61K 45/06* (2013.01); *C07K 16/40* (2013.01); *A61K 39/39533* (2013.01); *C12N 9/1205* (2013.01); *C12N 15/1137* (2013.01)

(58) Field of Classification Search
CPC .... C12N 9/12; C12N 9/1205; C12N 15/1137; A61K 38/005; A61K 45/00; A61K 39/3955
See application file for complete search history.

(56) References Cited

U.S. PATENT DOCUMENTS

| 6,518,266 B1* | 2/2003 | Dhanoa et al. | 514/229.2 |
| 8,822,447 B2* | 9/2014 | Zhang | C07D 231/56 514/210.18 |
| 2013/0209484 A1* | 8/2013 | Garcia et al. | 424/158.1 |

FOREIGN PATENT DOCUMENTS

| JP | 2007/284387 A | 11/2007 |
| WO | 01/07413 A1 | 2/2001 |
| WO | WO 2008024902 A2 * | 2/2008 |

OTHER PUBLICATIONS

Raushel FM et al. (1977) Bovine liver fructokinase: purification and kinetic properties. Biochemistry, 16(10):2169-75 (Abstract only).*
Coyle P et al. (2003) Zinc inhibition of hepatic fructose metabolism in rats. Biol. Trace Elem. Res. 92, 41-53.*
Ogawa T & Mimura Y (1999) Antioxidant effect of zinc on acute renal failure induced by ischemia-reperfusion injury in rats. Am. J. Nephrol. 19:609-614.*
Yagihasi S et al. (2010) The role of the polyol pathway in acute kidney injury caused by hindlimb ischemia in mice. J. Pathol. 220:530-541.*
Presentation Slides from interview on Mar. 18, 2016.*
Cirillo, Pietro et al., "Ketohexokinase-dependent metabolism of fructose induces proinflammatory mediators in proximal tubular cells", J. Am. Soc. Nephrol., 2009, vol. 20, No. 3, pp. 545-553.
Diggle, Christine P. et al., "Ketohexokinase: expression and localization of the principal fructose-metabolizing enzyme", Journal of Histochemistry & Cytochemistry, 2009, vol. 57, No. 8, pp. 763-774.
Asipu, et al., "Properties of normal and mutant recombinant human ketohexokinases and implications for the pathogenesis of essential fructosuria", Diabetes, 2003, vol. 52, No. 9, pp. 2426-2432.
International Search Report and Written Opinion, PCT/US2011/046938, Apr. 26, 2012.
Johnson RJ, Perez-Pozo SE, Sautin YY, Manitius J, Sanchez-Lozada LG, Feig DI, et al. Hypothesis: could excessive fructose intake and uric acid cause type 2 diabetes? Endocr Rev. Feb. 2009;30(1):96-116.
Stanhope KL, Schwarz JM, Keim NL, Griffen SC, Bremer AA, Graham JL, et al. Consuming fructose-sweetened, not glucose-sweetened, beverages increases visceral adiposity and lipids and decreases insulin sensitivity in overweight/obese humans. The Journal of clinical investigation. May 2009;119(5):1322-34.
Nakagawa T, Hu H, Zharikov S, Tuttle KR, Short RA, Glushakova O, et al. A causal role for uric acid in fructose- induced metabolic syndrome. American journal of physiology. Mar. 2006;290(3):F625-31.
Perez-Pozo SE, Schold J, Nakagawa T, Sanchez-Lozada LG, Johnson RJ, Lillo JL. Excessive fructose intake induces the features of metabolic syndrome in healthy adult men: role of uric acid in the hypertensive response. Int J Obes (Lond). Dec. 22, 2009.

(Continued)

*Primary Examiner* — Kimberly A. Ballard
(74) *Attorney, Agent, or Firm* — Timothy H. Van Dyke; Beusse, Wolter, Sanks & Maire, PLLC

(57) ABSTRACT

The invention relates to the use of isoform-specific fructokinase (ketohexokinase) (KHK) inhibitors alone or in combination with various agents to both prevent and treat a wide variety of diseases including, but not limited to, sugar craving, obesity, features of metabolic syndrome (including insulin resistance, hypertriglyceridemia, hypertension, and fatty liver), polyuria, proximal tubular injury, and diabetic kidney disease.

8 Claims, 7 Drawing Sheets

(56) References Cited

OTHER PUBLICATIONS

Roncal CA, Reungjui S, Sanchez-Lozada LG, Mu W, Sautin YY, Nakagawa T, et al. Combination of Captopril and Allopurinol Retards Fructose-Induced Metabolic Syndrome. American journal of nephrology. Aug. 21, 2009;30 (5):399-404.

Tran LT, Yuen VG, McNeill JH. The fructose-fed rat: a review on the mechanisms of fructose-induced insulin resistance and hypertension. Mol Cell Biochem. Jun. 18, 2009.

Segal MS, Gollub E, Johnson RJ. Is the fructose index more relevant with regards to cardiovascular disease than the glycemic index? European journal of nutrition. Oct. 2007;46(7):406-17.

Lee HT, Jan M, Bae SC, Joo JD, Goubaeva FR, Yang J, et al. A1 adenosine receptor knockout mice are protected against acute radiocontrast nephropathy in vivo. American journal of physiology. Jun. 2006;290(6):F1367-75.

Teff KL, Elliott SS, Tschop M, Kieffer TJ, Rader D, Heiman M, et al. Dietary fructose reduces circulating insulin and leptin, attenuates postprandial suppression of ghrelin, and increases triglycerides in women. The Journal of clinical endocrinology and metabolism. Jun. 2004;89(6):2963-72.

Cha SH, Sekine T, Fukushima JI, Kanai Y, Kobayashi Y, Goya T, et al. Identification and characterization of human organic anion transporter 3 expressing predominantly in the kidney. Mol Pharmacol. May 2001;59(5):1277-86.

Adelman RC, Ballard FJ, Weinhouse S. Purification and properties of rat liver fructokinase. J Biol Chem 1967;242 (14):3360-5.

de Araujo IE, Oliveira-Maia AJ, Sotnikova TD, Gainetdinov RR, Caron MG, Nicolelis MA, et al. Food reward in the absence of taste receptor signaling. Neuron. Mar. 27, 2008;57(6):930-41.

Park SH, Choi HJ, Lee JH, Woo CH, Kim JH, Han HJ. High glucose inhibits renal proximal tubule cell proliferation and involves PKC, oxidative stress, and TGF-beta 1. Kidney international. May 2001;59(5):1695-705.

Shapiro A, Mu W, Roncal C, Cheng KY, Johnson RJ, Scarpace PJ. Fructose-induced leptin resistance exacerbates weight gain in response to subsequent high-fat feeding. American journal of physiology. Nov. 2008;295(5):R1370-5.

Shapiro A, Turner N, Gao Y, Cheng KY, Scarpace PJ. Prevention and reversal of diet-induced leptin resistance with a sugar-free diet despite high fat content. The British journal of nutrition. Mar. 22, 2011:1-8.

Sanchez JJ, Gonzalez NS, Pontis HG. Fructokinase from rat liver. I. Purification and properties. Biochim Biophys Acta 1971;227(1):67-78.

Gersch MS, Mu W, Cirillo P, Reungjui S, Zhang L, Roncal C, et al. Fructose, but not dextrose, accelerates the progression of chronic kidney disease. American journal of physiology. Oct. 2007;293(4):F1256-61.

Nakayama T, Kosugi T, Gersch M, Connor T, Sanchez-Lozada LG, Lanaspa MA, et al. Dietary fructose causes tubulointerstitial injury in the normal rat kidney. American journal of physiology. Mar. 2010;298(3):F712-20.

Tappy L, Le KA. Metabolic effects of fructose and the worldwide increase in obesity. Physiol Rev. Jan. 2010;90(1):23-46.

Petrash JM. All in the family: aldose reductase and closely related aldo-keto reductases. Cell Mol Life Sci. Apr. 2004;61(7-8):737-49.

Gilbert RE, Cooper ME. The tubulointerstitium in progressive diabetic kidney disease: more than an aftermath of glomerular injury? Kidney international. Nov. 1999;56(5):1627-37.

Jiminez, Carola A. Roncal et al., "Fructokinase activity mediates dehydration-induced renal injury", Kidney International, 2014, vol. 86, pp. 294-302.

Lanaspa, Miguel A., "Endogenous Fructose Production and Fructokinase Activation Mediate Renal Injury in Diabetic Nephropathy", J Am Soc Nephrol, 2014, vol. 25, pp. 1-13.

Ishimoto, Takuji et al, "Opposing effects of fructokinase C and A isoforms on fructose-induced metabolic syndrome in mice", PNAS, 2012, vol. 109(11), pp. 4320-4325.

\* cited by examiner

METHODS AND COMPOSITIONS FOR THE INHIBITION OF FRUCTOKINASE

CROSS REFERENCE TO RELATED APPLICATIONS

This application claims priority to U.S. Provisional Application No. 61/371,255, filed Aug. 6, 2010, which is incorporated herein in its entirety.

GOVERNMENTAL SUPPORT

This invention was made with government support under grant number HL068607 awarded by the National Institutes of Health. The government has certain rights in the invention.

FIELD OF THE INVENTION

The present inventors have identified fructokinase as a key enzyme that drives a host of metabolic conditions characterized by sugar craving, obesity, metabolic syndrome, and renal disease. In particular, isoform specific inhibitors targeting fructokinase C, or both fructokinase A and C, or stimulation of fructokinase A with or without other therapeutic agents, will be an effective treatment of these conditions.

BACKGROUND OF THE INVENTION

Fructokinase (ketohexokinase, KHK) is a key enzyme in fructose metabolism, and phosphorylates fructose to fructose-1-phosphate. In turn, fructose 1-phosphate is metabolized by aldolase B and triokinase to dihydroxyacetone phosphate and glyceraldehyde 3-phosphate, which leads eventually to glycolysis and the generation of triglycerides. Two major isoforms of fructokinase exist, consisting of fructokinase C (KHK-C), which is the principal fructokinase isoform present in small intestine, liver and kidney, and fructokinase A (KHK-A), which is expressed in most tissues, and especially in skeletal muscle.

Recent studies suggest that excessive ingestion of fructose, primarily in the form of added sugars, such as high fructose corn syrup (HFCS) and sucrose, may have a role in the epidemic of obesity and diabetes.[1-2] The administration of high concentrations of fructose to animals[3] and to humane[2, 4] can induce features of metabolic syndrome, including insulin resistance, hypertriglyceridemia, low HDL cholesterol, fatty liver, and elevated blood pressure. These features are not seen in subjects administered equivalent amounts of glucose or starch.[2] These types of studies, as well as experiments in animal models, have clearly demonstrated that the effects of fructose to induce metabolic syndrome are independent of excessive energy intake.[5]

Further, all animals like sugar (sucrose), as the stimulation of sweet taste causes a feeling of pleasantness as a consequence of stimulating dopamine in the brain.[1-2] In addition to sucrose, other sweet substances, such as glucose, fructose, and artificial sugars (sucralose) can also stimulate dopamine responses. However, it has been shown that the repeated ingestion of sugar in mice can lead to a craving or addiction syndrome. These animals develop features similar to that observed with drug addiction, and will show signs of anxiety or withdrawal following elimination of sugar from the diet or the administration of naloxone.[3-4] The mechanism appears to relate to a reduction in dopamine receptors (especially D2 receptors) in the nucleus accumbens from chronic dopamine stimulation, leading to a loss of control mechanisms in the frontal and prefrontal cortex.[5] The importance of this pathway is being increasingly recognized as a mechanism that results in lack of normal control, and may have a role in the pathogenesis of obesity, attention deficit hyperactivity disorder, and even aggressive behavior and dementia.[2, 6-10] Thus, identifying a way to prevent the craving for sugar might be of great benefit in reducing the frequency of these conditions.

Fructose has also been shown to induce leptin resistance and to encourage increased food intake in rats.[9] Others have also suggested fructose may not quench satiety, either based on effects on systemic release of insulin and ghrelin[10] or as a consequence of central effects.[11] Thus, fructose ingestion may cause weight gain.

The mechanism by which fructose induces metabolic syndrome is not completely known, but appears to be mediated by the ability of fructose to raise uric acid levels, and induce endothelial dysfunction and oxidative stress.[3, 6] Since the generation of uric acid occurs during the phosphorylation of fructose by fructokinase, we have postulated that fructokinase is responsible for the development of metabolic syndrome in response to fructose.[1, 7]

To date, studies inhibiting fructokinase are limited. We reported that the metabolism of fructose by fructokinase in kidney proximal tubular cells could produce a prooxidative response with the generation of uric acid and inflammatory mediators.[8] Knocking down fructokinase with a specific siRNA was able to block this proinflammatory response.[8]

While the above studies suggest fructokinase may have important roles in metabolic syndrome, we have identified several novel roles for fructokinase and its isoforms which constitute the basis for this patent application.

SUMMARY OF THE INVENTION

Our recent studies have identified additional roles for KHK that were not previously noted in the literature.

The first relates to our discovery that KHK, and in particular, KHK-C, has an important role in sugar craving (defined as a craving for sucrose or high fructose corn syrup (HFCS)). Sugar craving is a distinct process and consists of a specific desire for sugar. It has been shown to be mediated by dopaminergic signaling in the brain and is similar to the addictive response one can observe with narcotics.[12] It had been thought to be mediated by taste receptors, but when the taste receptor signaling is blocked, craving for sugar still occurs.[13] Thus, the specific mechanism responsible for sugar craving had been unknown.

The second discovery is that the inhibition of KHK also prevents fat accumulation in response to fructose. In this regard, while fructose has been postulated to have a role in metabolic syndrome via KHK, its ability to induce obesity has been difficult to show in experimental animals, and the role of KHK in this process has not been proven.[9] In contrast, the present inventors have found that mice lacking KHK-C and KHK-A are protected from fructose-induced fat gain and also maintain a leaner body mass. In addition to the observation that inhibition of KHK-C, or the combination of KHK-C and KHK-A, can block obesity from dietary fructose, we also had the surprising discovery that mice lacking KHK-C and KHK-A are protected from obesity induced by supplementing drinking water with glucose. In essence, drinking glucose resulted in activation of aldose reductase (AR) of the polyol pathway, which converts glucose to sorbitol, and is then converted by sorbitol dehydrogenase (SDH) to fructose. The endogenous fructose is then metabolized by KHK with the generation of byproducts, such as uric acid that stimulates fat accumulation.

The use of KHK-C inhibitors may thus provide a variety of benefits. First, they are a useful treatment for subjects trying to lose weight who have problems with sugar craving. It will also be a useful adjunct to help reduce sugar intake from fructose containing sugars, and hence should have benefits on metabolic syndrome, obesity, fatty liver, and chronic kidney disease. Finally, it will also help subjects lose weight even if they are on a sugar- or fructose-free diet, by blocking the effects of endogenously produced fructose from dietary carbohydrates.

In addition, the present inventors have surprisingly found that the mechanism by which acute and chronic tubular renal injury from a host of conditions result from activation of fructokinase-C (KHK-C). In particular, the present inventors have surprisingly found that the endogenous production of fructose is not a benign process, but rather can lead to substantial injury in cells that express or overexpress fructokinase-C (KHK-C). While not wishing to be bound by theory, it is believed that the rise in proximal tubular glucose levels activates aldose reductase (AR) of the polyol pathway, which converts glucose to sorbitol, and is then converted by sorbitol dehydrogenase (SDH) to fructose.

In most kidney cells the metabolism ends here, but the S3 segment of the proximal tubule is unique from other kidney cells by having constitutive levels of fructokinase C (ketohexokinase, KHK-C). KHK-C is distinct from other enzymes involved in sugar metabolism in that it phosphorylates fructose rapidly, leading to transient ATP depletion, adenine nucleotide turnover, and uric acid production. In turn, uric acid will act as an oxidant stimulating the synthesis of MCP-1, a chemokine for recruitment and activation of macrophages. The tubular cell may swell as a result of the ATP depletion, begin to lose its brush border, and/or the local inflammatory response may lead to injury to the microvasculature. If the injury is mild, it produces polyuria and a Fanconi-like syndrome, as the functions of the brush border functions are impaired. If the injury is severe, acute tubular cell loss and acute kidney injury (AKI) may develop. If the injury is chronic, low grade tubulointerstitial fibrosis may develop.

In a subject with diabetes, it is believed that AR, SDH, and KHK-C are upregulated by increased urinary osmolarity from glycosuria. Further, in a subject who has undergone radiocontrast administration, it is believed that the same enzymes are upregulated due to the effects of the contrast agent. In settings such as sepsis, or following cardiovascular surgery, the same enzymes are upregulated due to the effects of ischemia. The present inventors have also found that radiocontrast agents, which are known to be nephrotoxic, may cause renal tubular injury as a consequence of activating aldose reductase, followed by activation of KHK in association with the normal high glucose flux occurring through the cell. Accordingly, diabetic wild type mice administered contrast agents developed acute kidney injury, but this was not observed in diabetic KHK knockout mice.

The methods and compositions comprising a KHK-C (KHK-C or KHK-A and KHK-C) inhibitor as described herein are suitable, individually or combination, for the treatment of any disorder or physical condition characterized by an increased presence or activity of at least KHK-C. In one embodiment, the disorder or physical condition characterized by an increased presence or activity of KHK-C, as well as KHK-A.

Exemplary disorders to be treated or prevented by the compositions and methods described herein include, but are not limited to, renal injury, which includes but is not limited to any form of acute or chronic renal tubular injury such as acute kidney injury (AKI) associated with administration of a contrast agent, AKI associated with cardiovascular surgery or sepsis, or the like. In addition, the methods and compositions described herein may be or may also be utilized in the treatment or prevention of, attention deficit disorder or attention deficit hyperactivity disorder (collectively "attention deficit disorder"), sugar addiction, obesity, metabolic syndrome, fatty liver, diabetic polyuria, diabetic nephropathy, and/or other addiction-related behavior of a mammal. In further embodiments, the compositions and methods described herein may be or may also be administered to a subject to provide a diminished craving in the subject for fructose and/or fructose-containing sugars; to reduce body mass index; or to improve kidney function. As set forth herein, the methods and compositions described herein may be administered to a subject as the single therapy or along with a conjunctive therapeutic agent, which is administered to a subject to treat or prevent the same or distinct disorder or physical condition as the KHK inhibitor.

BRIEF DESCRIPTION OF THE DRAWINGS

The invention is explained in the following description in view of the drawings that show.

DETAILED DESCRIPTION OF THE INVENTION

Figure 1:
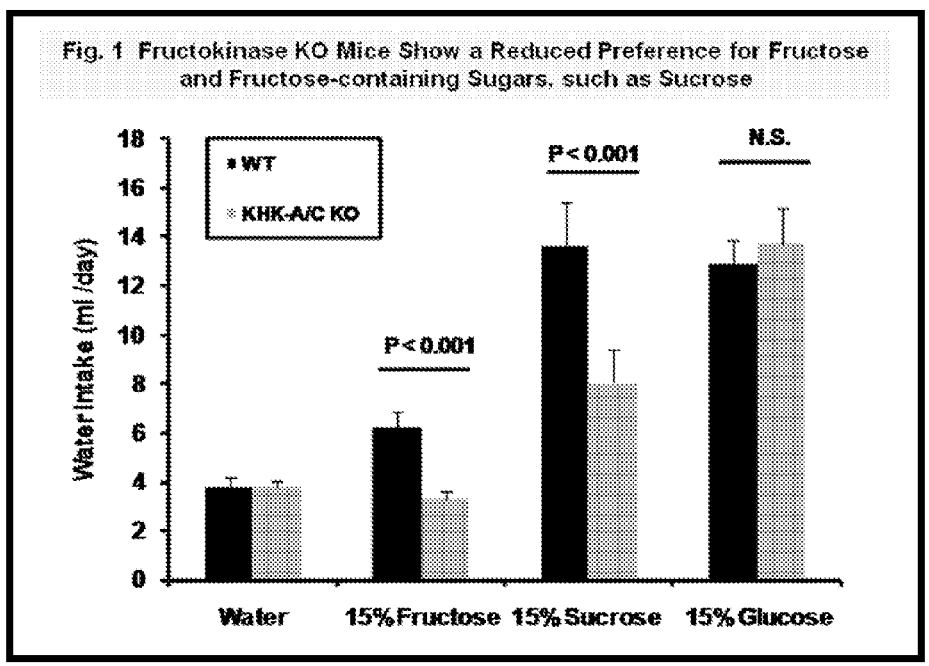
FIG. 1 illustrates that KHK-A/C KO (knockout) mice show no preference for fructose-containing water, reduced preference for fructose-containing sugars such as sucrose, and continued preference for drinking water containing glucose compared to wild type (WT) mice.

The specifics of the discovery include the use of an agent that can specifically inhibit KHK C, or both KHK C and KHK A, to treat specific conditions as outlined below.

DEFINITIONS

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "co-administered, "co-administering," or "concurrent administration", when used, for example with respect to administration of a conjunctive agent along with administration of a KHK-C inhibitor refers to administration of the KHK-C inhibitor and the conjunctive agent such that both can simultaneously achieve a physiological effect. The two agents, however, need not be administered together. In certain embodiments, administration of one agent can precede administration of the other, however, such co-administering typically results in both agents being simultaneously present in the body (e.g. in the plasma) of the subject.

As used herein, the terms "diabetic" or "diabetes" refers to Type 1 diabetes, wherein the pancreas produces little or no insulin; Type 2 diabetes, wherein the body becomes resistant to the effects of insulin or produces little or no insulin; or disease state occurring as sequelae of other primary diseases that include the symptoms of either or both of elevated blood sugar (hyperglycemia) and the excretion of sugar in the urine (glycosuria).

As used herein, the terms "disease," "disorder," or "complication" refers to any deviation from a normal state in a subject. In preferred embodiments, the methods and compositions of the present invention are useful in the diagnosis and treatment of diseases where the expression of a KHK protein differs between subjects with disease and subjects not having disease. The present invention finds use with any number of diseases including, but not limited to, renal diseases.

As used herein, by the term "effective amount," "amount effective," "therapeutically effective amount," or the like, it is meant an amount effective at dosages and for periods of time necessary to achieve the desired result. In the case of the co-administration of a KHK-C inhibitor with a conjunctive agent as described herein, the conjunctive agent, the KHK-C inhibitor, or the combination of the KHK-C inhibitor and the conjunctive agent may supply the effective amount.

As used herein, the term "expression" in the context of a gene or polynucleotide involves the transcription of the gene or polynucleotide into RNA. The term may also, but not necessarily, involve the subsequent translation of the RNA into polypeptide chains and their assembly into proteins.

As used herein, the terms "interfering molecule" refer to all molecules, e.g., RNA or RNA-like molecules, which have a direct or indirect influence on gene expression, such as the silencing of a target gene sequence. Examples of other interfering RNA molecules include siRNAs, short hairpin RNAs (shRNAs), single-stranded siRNAs, microRNAs (miRNAs), methylated siRNAs or other siRNAs treated to protect the siRNA from degradation by circulating RNases, and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, and dicer-substrate 27-mer duplexes are subsets of "interfering molecules." "Interfering molecules" also may include PMOs.

As used herein, the terms "phosphothioate morpholino oligomer(s)," "a PMO" or "PMOs" refer to molecules having the same nucleic acid bases naturally found in RNA or DNA (i.e. adenine, cytosine, guanine, uracil or thymine), however, they are bound to morpholine rings instead of the ribose rings used by RNA. They may also linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits.

As used herein, the term "antisense sequence" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these.

As used herein, the term "RNA interference" (RNAi) refers to a post-transcriptional gene silencing (PGSR) process whereby one or more exogenous small interfering RNA (siRNA) molecules are used to silence expression of a target gene.

As used herein, "siRNAs" (short interfering RNAs) refer to double-stranded RNA molecules, generally around 15-30 nucleotides in length, that are complementary to the sequence of the mRNA molecule transcribed from a target gene.

As used herein, "shRNAs" (small hairpin RNAs) are short "hairpin-turned" RNA sequences that may be used to inhibit or suppress gene expression.

As used herein, a "composition," "pharmaceutical composition" or "therapeutic agent" all include a composition comprising at least a KHK-C inhibitor. Optionally, the "composition," "pharmaceutical composition" or "therapeutic agent" further comprises pharmaceutically acceptable diluents or carriers. In the case of an interfering molecule, for example, the interfering molecule may be combined with one or more pharmaceutically acceptable diluents, such as phosphate-buffered saline, for example. As used herein, a pharmaceutical composition particularly refers to a composition comprising at least a KHK-C inhibitor that is intended to be administered to a subject as described herein.

As used herein, the term "KHK-C inhibitor" includes an inhibitor that selectively inhibits KHK-C or both KHK-A and KHK-C.

As used herein, the term "KHK" refers KHK-A and KHK-C unless otherwise specified.

As used herein, the term "preventing" means causing the clinical symptoms of the disease state not to develop, e.g., inhibiting the onset of disease, in a subject that may be exposed to or predisposed to the disease state, but does not yet experience or display symptoms of the disease state.

As used herein, the terms "contrast agent" or "radiocontrast agent" refer to a medical contrast medium used to improve the visibility of internal bodily structures in x-ray based imaging techniques such as computed tomography (CT) and radiography. In one embodiment, the radiocontrast agent comprises an iodine or barium compound, including, but not limited to, diatrizoate or diatrizoic acid, metrizoate, ioxaglate, iopamidol, iohexyl, ioxilan, iopomide, iodixanol, or combinations thereof.

As used herein, the term "subject" refers to any animal (e.g., a mammal), including, but not limited to, humans, non-human primates, rodents, and the like, which is to be the recipient of a particular treatment.

As used herein, the terms "treating" or "treatment" or "alleviation" refers to both therapeutic treatment and prophylactic or preventative measures, wherein the object is to prevent or slow down (lessen) the targeted pathologic condition or disorder.

Chapter 1: Fructokinase Inhibition for Sugar Craving, Obesity, and Attention Deficit Disorder, and Metabolic Syndrome The mechanism by which sugar craving occurs has remained a mystery. It was originally thought that there might be a major role for taste receptors, but when taste receptor signaling is blocked, sugar (sucrose) still induces a robust dopamine response in the brain, whereas artificial sugars do not.[15] The present inventors have shown that the craving for fructose and sugar (sucrose) is dependent on fructokinase. Specifically, fructokinase knockout mice (KHK-A/C KO mice) show no preference of water containing 15% fructose over drinking water alone, and they also show a 50% reduction in intake of sucrose drinking water. In contrast, KHK-A/C KO (knockout) mice continue to show preference for drinking water containing glucose (FIG. 1).

These studies show that blocking fructokinase can block craving of fructose, and also reduce the craving for fructose-containing sugars, such as high fructose corn syrup and sucrose. Since sugar craving is a manifestation of sugar addiction, which is thought to have a major role in causing obesity, food-associated addiction disorders, and attention deficit hyperactivity deficit syndrome, the use of fructokinase inhibitors will be able to be an adjunctive treatment for these disorders In accordance with one aspect of the present invention, there are provided methods and compositions comprising KHK-C inhibitors for blocking fructokinase (KHK-A and KHK-C, or KHK-C only) to correspondingly block the craving of fructose-containing sugars, including fructose alone, sucrose, high fructose corn syrup, or invert sugar. The craving for sugars that can be converted to fructose in the body, such as sorbitol, will also be blocked.

In accordance with another aspect of the present invention, since repeated sugar intake from craving can induce obesity, there are provided methods and compositions comprising KHK-C inhibitors that are able to block sugar addiction syndromes and hence be an adjunctive treatment for obesity.

In accordance with another aspect of the present invention, there is provided a method for reducing a craving for fructose and/or fructose-containing sugars in a subject, the method comprising inhibiting KHK-C activity in the subject. In one embodiment, the method comprises administering a KHK-C inhibitor to the subject.

In accordance with another aspect of the present invention, there is provided a composition useful for decreasing a craving for fructose and/or a fructose-containing compound, the composition comprising a KHK-C inhibitor.

In accordance with yet another aspect of the present invention, since sugar intake from sugar craving is likely a major cause of attention deficit disorder or attention deficit hyperactivity disorder (collectively "attention deficit disorder"), there are provided methods and compositions comprising KHK inhibitors for blocking fructokinase to prevent or treat attention deficit hyperactivity disorder. Such inhibitors will also be a useful adjunctive treatment in children and adults diagnosed with attention deficit hyperactivity disorder or in which the patients' physician is concerned may be manifesting symptoms worrisome for the development of attention deficit hyperactivity disorder, including but not limited to the presence of inattention, difficulty concentration, and the like.

In accordance with another aspect of the present invention, there is provided a method for treating or preventing attention deficit disorder, a sugar addiction, obesity, and/or metabolic syndrome. The method comprises administering to the subject a KHK-C inhibitor. A composition for treating or preventing attention deficit disorder, a sugar addiction, obesity, and/or metabolic syndrome may likewise be provided.

In accordance with another aspect of the present invention, there is provided a method of treating fatty liver in a subject. The method comprises inhibiting KHK-C, or both KHK-A and KHK-C in the subject. A composition for treating fatty liver may likewise be provided:

In accordance with another aspect of the present invention, there is provided a method for diminishing, inhibiting or eliminating addiction-related behavior of a subject, wherein said method comprises administering a composition comprising a KHK-C inhibitor (to inhibit KHK-C or both KHK-A and KHK-C) to the subject, and wherein the addiction-related behavior is associated with a compulsion for fructose and/or sucrose intake. A composition for diminishing, inhibiting or eliminating addiction-related behavior of a mammal comprising a KHK-C inhibitor may likewise be provided.

Chapter 2: Fructokinase Inhibition for Obesity

Fructose is a sugar present in honey and fruits, but also is a major component of a variety of sugars, most notably sucrose (where constitutes 50% of the sugar), and high fructose corn syrup. Studies have shown that the administration of fructose or fructose-containing sugars can induce obesity in animals, which is likely by inducing leptin resistance and blocking normal satiety mechanisms.[16-17]

Figure 2:
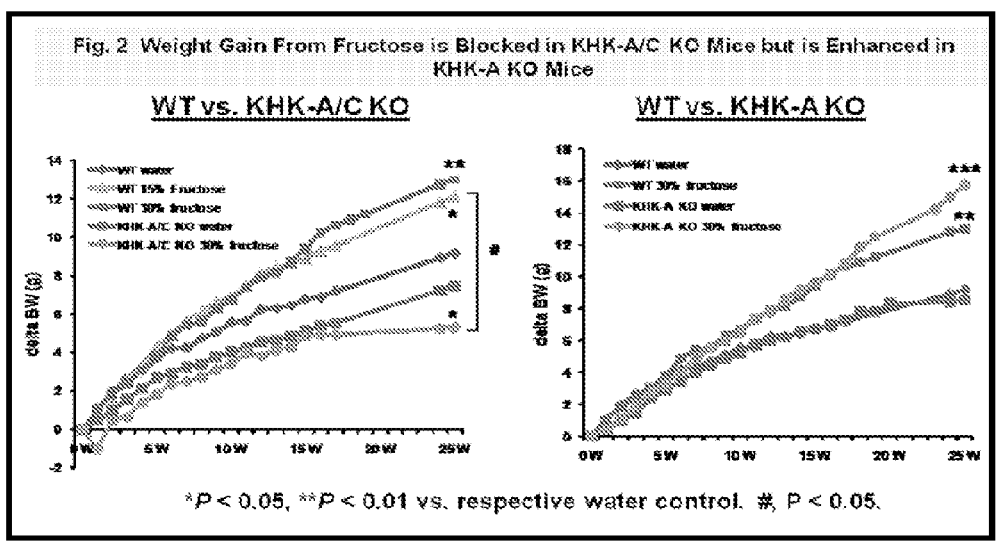
FIG. 2 includes graphs showing that mice lacking only KHK-A (KHK-A KO) are not protected from obesity but rather show enhanced weight gain when fed either fructose in their drinking water (as either a 15% or 30% solution) for 25 weeks compared to wild type (WT) mice.

The present inventors have made two novel discoveries that were not predicted based on the currently published literature. First, the inventors have discovered that the extent to which obesity from fructose is treated or prevented in a subject depends on which fructokinase isoform is blocked, KHK-A or KHK-C. Most authorities had thought KHK-C was the only KHK isoform that actively metabolizes fructose. However, the present inventors recently found that whereas mice lacking both KHK isoforms (KHK-A/C KO) do not develop fructose induced obesity, mice lacking only KHK-A (KHK-A KO) are not protected from obesity but rather show enhanced weight gain when fed either fructose in their drinking water (as either a 15% or 30% solution) for 25 weeks (FIG. 2).

Figure 3:
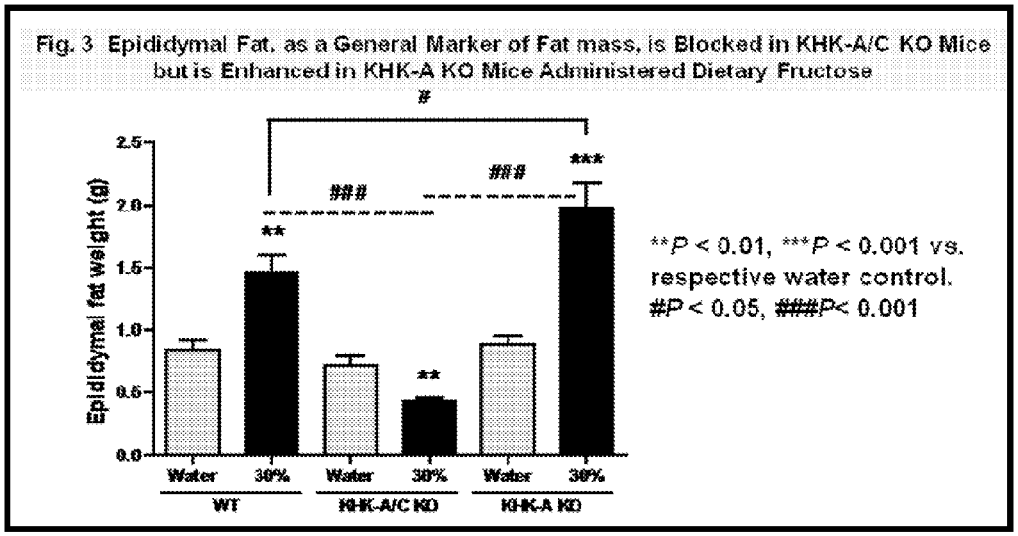
FIG. 3 includes graphs showing epididymal fat as a general marker of fat mass is increased in wild type (WT) mice given fructose, but the increase in fat is prevented in KHK-A/C KO mice, but is enhanced in KHK-A KO mice administered daily fructose.
Figure 4:
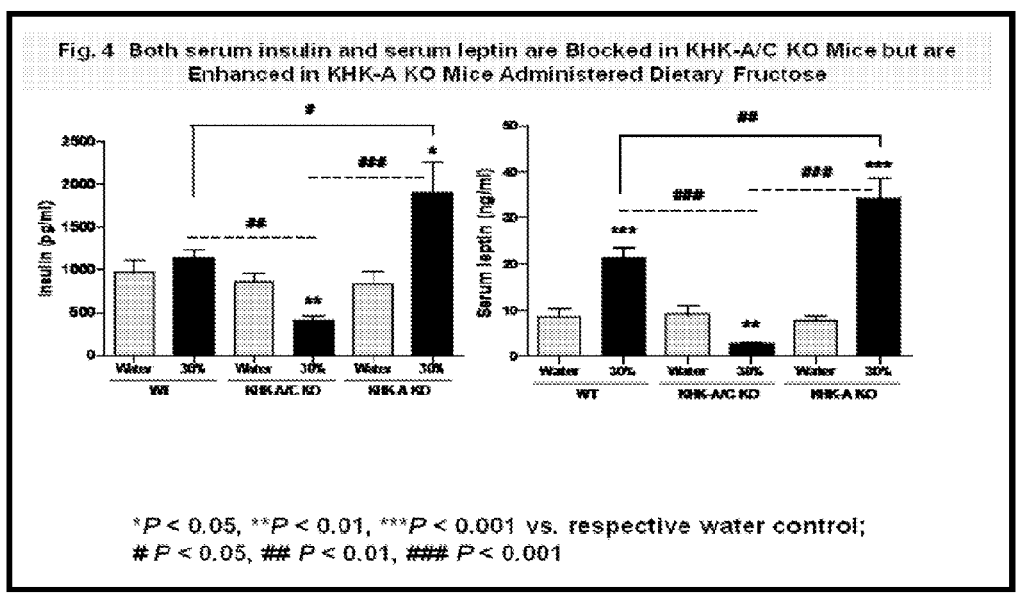
FIG. 4 includes graphs showing that both serum insulin and serum leptin are increased in wild type (WT) mice given fructose, but these increases are prevented in KHK-NC KO mice, and are enhanced in KHK-A KO mice administered dietary fructose.
Figure 5:
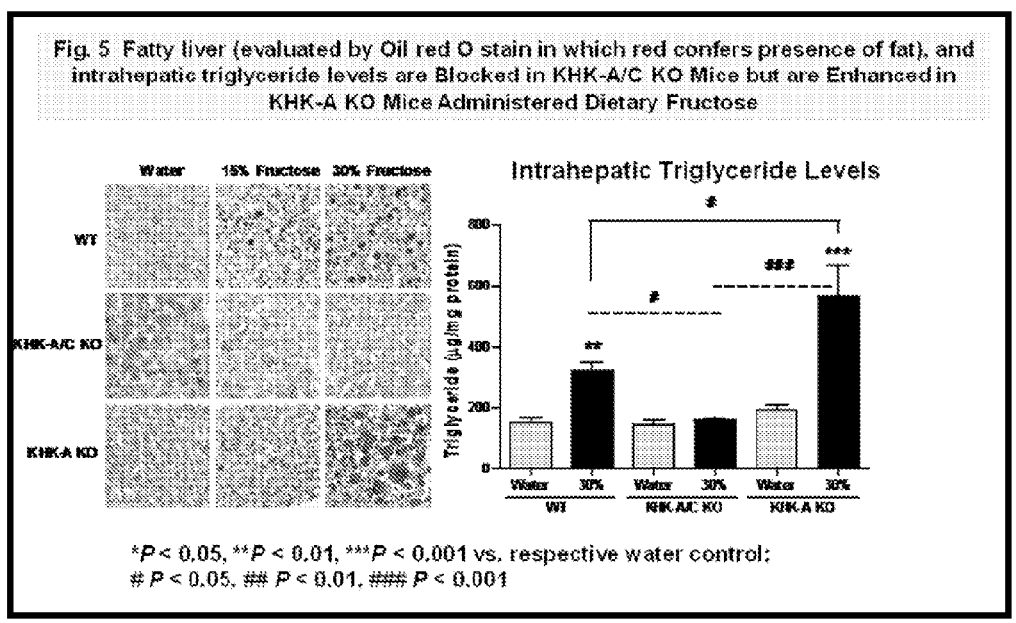
FIG. 5 shows that fat and intrahepatic triglyceride levels are increased in wild type (WT) mice given fructose. These effects are prevented in KHK-A/C mice, but are enhanced in KHK-A KO mice administered dietary fructose.

Further, the present inventors have also shown that mice lacking both KHK isoforms (KHK-A and KHK-C) are protected from increased body fat, insulin resistance (hyperinsulinemia), elevated serum leptin levels (a measure of leptin resistance) and fatty liver, whereas KHK-A knockout mice showed worse fat accumulation, higher insulin and leptin levels, and fatty liver compared to wild type mice fed fructose (FIGS. 3-5). These studies document that to prevent or treat dietary fructose-induced obesity, one must either block both KHK isoforms, block KHK-C, or stimulate KHK-A.

Moreover, the present inventors have found that KHK-C inhibitors will also be useful in preventing obesity from glucose or starch based foods that do not contain fructose or fructose-containing sugars. This is due to the fact there is a large amount of fructose is generated endogenously in the absence of dietary fructose, likely from the polyol pathway that converts glucose to fructose. While the presence of the polyol pathway had been known, it has largely been thought to have a minor role in nondiabetic individuals where it has been thought to account for only 1% of the overall glucose metabolism. Furthermore, the primary effects of the polyol pathway had been attributed to the production of sorbitol, and a role for fructose in mediating toxicity from the polyol pathway had not been considered. Indeed, the polyol pathway has also not been considered to be involved in the pathogenesis of obesity until the present invention.

Figure 6:
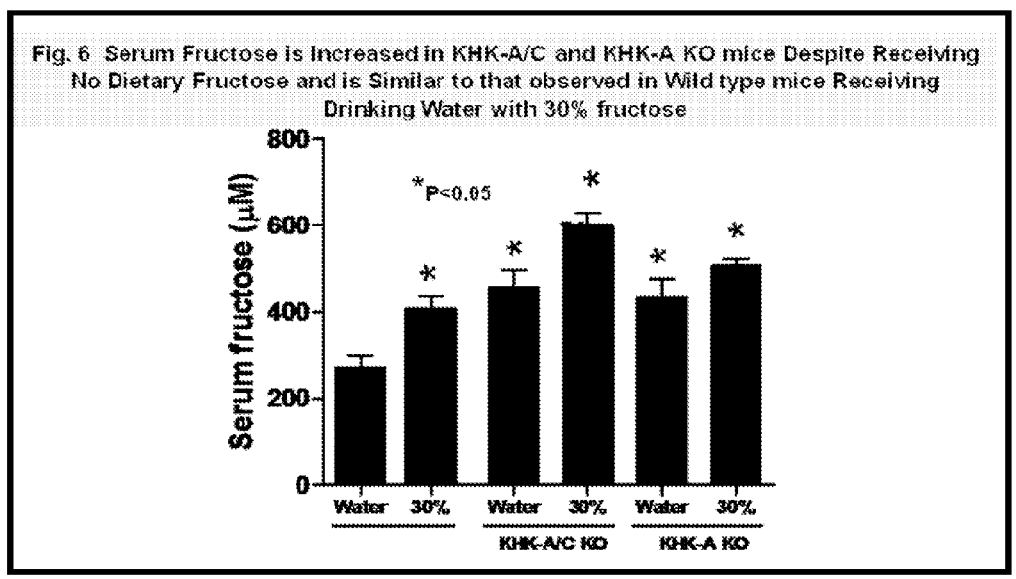
FIG. 6 shows that serum fructose is increased in both KHK-AC KO and KHK-A KO mice despite receiving no dietary fructose and is similar to that observed in wild type mice receiving drinking water with 30% fructose.
Figures 7A, 7B, 7C, 7D, 7E, 7F:
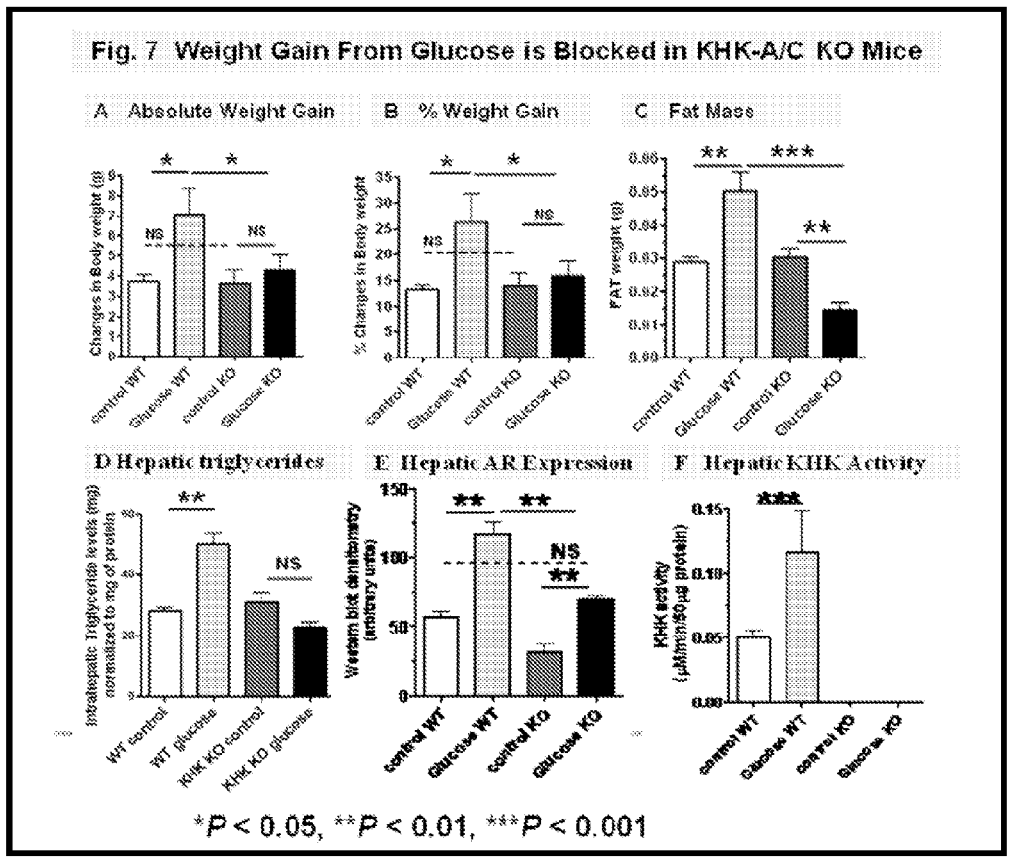
FIGS. 7A-7F show that the increased fat mass and intrahepatic triglycerides observed in wild type (WT) mice given glucose are blocked in KHK-NC KO mice and that aldose reductase (AR) expression is increased in glucose fed WT mice as well as hepatic KHK activity.

The studies performed by the present inventors showed that in mice lacking either both fructokinase isoforms (KHK-A/C KO mouse) or the fructokinase A isoform (KHK-A KO mouse), there is a spontaneous increase in serum fructose levels that is similar to that observed in wild type mice receiving drinking water supplemented with 30% fructose, the latter which corresponds to a diet in which over 40% of the total calories are from fructose. The observation that both the KHK-NC KO and KHK-A KO mouse have such high serum fructose levels despite a diet that contains no fructose shows that KHK is involved in the metabolism of a large endogenous pool of fructose (FIG. 6).

Moreover, the present inventors have found for the first time that there is a large amount of fructose being generated daily in the absence of dietary fructose. Since the only known source for endogenous fructose generation is from dietary glucose present in carbohydrates and starches, the mechanism by which carbohydrates may cause obesity could involve the production of endogenous fructose with metabolism via KHK.

As shown in FIGS. 7A-7F, mice fed glucose in their drinking water (30%) develop obesity, but both the absolute change in weight (FIG. 7A), the change in body weight (FIG. 7B), and the increase in epididymal fat mass as a reflection of total fat mass (FIG. 7C), as well as intrahepatic triglycerides as a measure of fatty liver (FIG. 7D) are prevented in KHK NC knockout (KO) mice. Furthermore, aldose reductase (AR) expression is increased in glucose fed WT mice (FIG. 7E) as well as hepatic KHK activity (FIG. 7F), documenting that glucose activates KHK activity likely via activation of AR in the liver. These data show a new indication for KHK inhibitors, which is to prevent obesity induced by carbohydrates and particularly glucose-containing carbohydrates.

In accordance with one aspect of the present invention, the KHK-C inhibitors described herein are useful as an adjunct treatment for obesity in subjects, such as subjects consuming large amounts of sugar, which according to the AHA is likely >50 or 75 g or more daily. Our studies also document that blocking KHK-C or KHK-A and KHK-C via KHK-C inhibitors as described herein will be useful for the general prevention and treatment of obesity even in subjects not ingesting fructose-containing sugars, since it is nearly impossible to maintain a diet that does not contain a substantial amount of carbohydrates. Thus, by blocking the carbohydrate pathway involved in obesity, the KHK-C inhibitors described herein may also be useful as an adjunctive agent to assist diets or medical or surgical treatments aimed at losing weight.

In accordance with another aspect of the present invention, there is provided a KHK inhibitor and method that blocks either both isoforms (KHK-A and KHK-C), blocks KHK-C, or stimulates KHK-A for the treatment and/or prevention of obesity disease. In one embodiment, the disease is obesity. By obesity, it is meant all dietary-induced obesity, including subjects on an absent, low sugar- or fructose-based diet. Importantly, since carbohydrates are a component of all diets, the use of this therapeutic agent comprising a KHK inhibitor will be of benefit for all forms of obesity. In one embodiment, there is provided a method of treating obesity independent of fructose intake in a subject. The method comprises inhibiting KHK-C in the subject, such as by administering a KHK-C inhibitor to the subject. A composition comprising a KHK-C inhibitor may likewise be provided.

In accordance with another aspect of the present invention, there is a provided a method of minimizing body mass index (BMI) in a subject. The method comprises inhibiting KHK-C in the subject, such as by administering a KHK-C inhibitor to the subject. A composition comprising a KHK-C inhibitor may likewise be provided.

Chapter 3: Fructokinase Inhibition for Acute and Chronic Renal Disease

We had previously reported that the administration of fructose in the diet can cause renal tubular injury in vitro[18] and also renal disease in rats[19-20]. Aspects of the present invention further relate to the discovery that fructokinase has a critical, role in many specific kidney diseases, including acute and chronic diabetic renal disease, and acute kidney injury from a wide variety of conditions including from radiocontrast, sorbitol administration (such as from the administration of IgG preparations containing sorbitol), ischemia reperfusion (such as following cardiovascular surgery), and sepsis. In none of these conditions was fructokinase ever considered to have a role. KHK C is an enzyme that is present primarily in the liver, intestine, and proximal tubule of the kidney.[21] The role of KHK (KHK-A and KHK-C) in the kidney has been largely unknown, and it had been thought to have a minor role in the metabolism of dietary fructose.[22] However, the proximal tubule is a site of extensive glucose absorption. Under normal conditions most of the glucose is absorbed into the blood stream unchanged, but it is known that glucose can be converted to fructose via the polyol pathway, in which glucose is first converted to sorbitol via aldose reductase (AR), followed by conversion to fructose via sorbitol dehydrogenasae (SDH).[22] Since AR and SDH are minimally expressed in the proximal tubule under normal conditions, very little endogenous (e.g., non-dietary) fructose is normally present.

Figure 8:
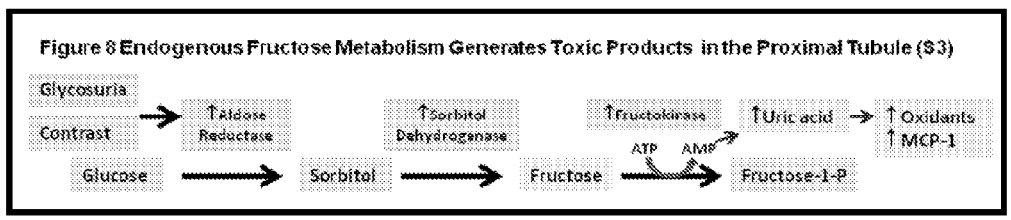
FIG. 8 is a schematic showing endogenous fructose metabolism in the proximal tubule.
Figures 9A, 9B, 9C, 9D:
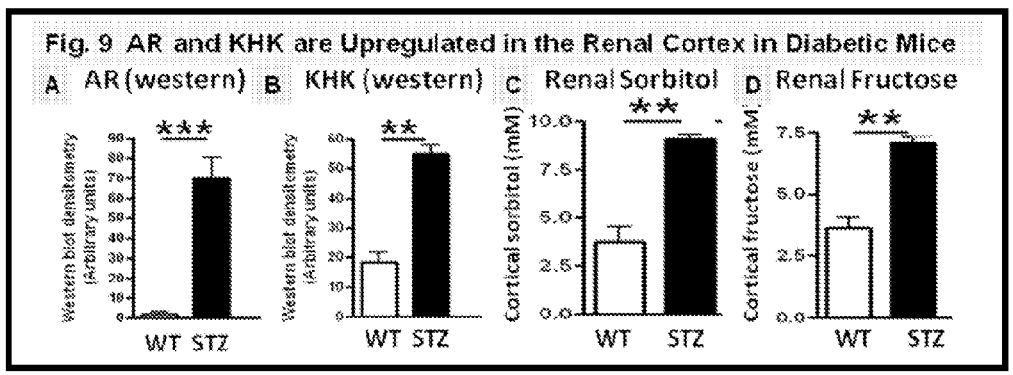
FIGS. 9A-9D show that aldose reductase (AR) and fructokinase (KHK) are upregulated in the renal cortex of diabetic mice.

However, AR can be increased by a variety of stimuli, including high glucose, high osmolality, and ischemia. This has led to studies suggesting that activation of AR in diabetes may contribute to kidney disease or other diabetic complications.[23] However, never was a role for KHK suspected in any of these studies, and most thought the toxicity, if present, was due to sorbitol. In one aspect of the present invention, the present inventors have found that a wide variety of renal diseases are mediated by KHK activation in the proximal tubule, in which the production of endogenous fructose in the proximal tubule activates KHK, leading to the generation of toxic downstream products (uric acid, oxidants, and monocyte chemoattractant protein-1 (MCP-1), that drive local renal injury (FIG. 8).

The compositions and methods described herein may be utilized for the treatment and prevention of acute and chronic diabetic renal diseases. Under normal conditions, aldose reductase (AR) is expressed in the renal medulla and not in the renal cortex where the proximal tubules are located. However, in diabetes, such as in mice with streptozotocin (STZ)-induced diabetes, AR and SDH are upregulated in the renal cortex compared to that observed in wild type (WT) mice, resulting in conversion of the glucose that is absorbed in the proximal tubule to sorbitol and fructose (FIGS. 9A-9D).

Figures 10A, 10B, 10C, 10D, 10E, 10F, 10G, 10H, 10I:
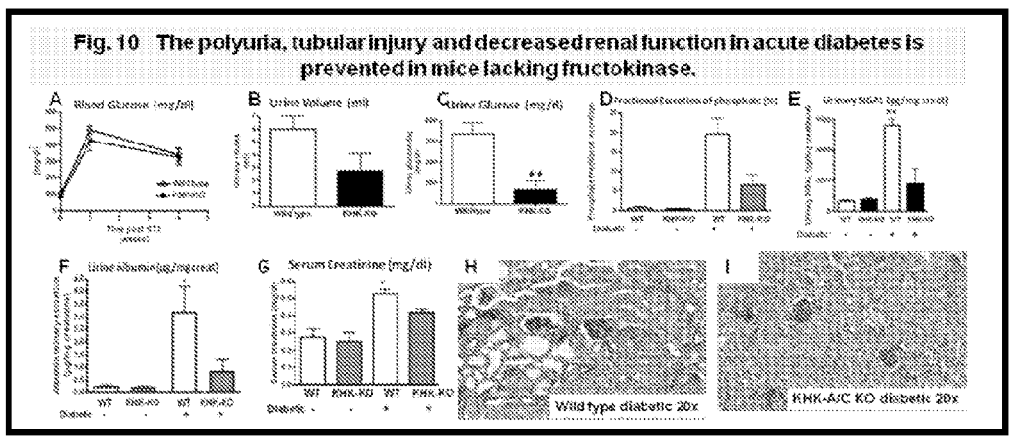
FIGS. 10A-10I show both wild type (WT) and fructokinase knockout (KHK-KO) mice had similar blood glucose levels following STZ injection (FIG. 10A), but KHK KO mice were protected from polyuria (FIG. 10B), glycosuria (FIG. 10C), phosphaturia (FIG. 10D), and tubular injury, as noted by urinary NGAL excretion (FIG. 10E) and urinary albumin excretion (FIG. 10F). The renal injury in the wild type mice was also associated with an increase in serum creatinine, documenting impaired renal function (FIG. 10G). Histologic injury, consisting of loss of brush border, vacuolization, tubular atrophy and proliferation, was also present in the diabetic wild type mice (FIG. 10H) but absent in the KHK KO mice (FIG. 1).

The increase in renal fructose should provide a substrate for KHK, for which we had previously shown converts fructose to fructose-1-phosphate with the generation of uric acid, oxidants, and inflammatory mediators such as monocyte chemoattractant protein-1 (MCP-1).[18] This leads to the local tubular injury. Consistent with this hypothesis, the present inventors have found that proximal tubular injury associated with acute diabetes was completely prevented in mice lacking both KHK isoforms (FIGS. 10A-10I). As shown in FIGS. 10A-10I, both wild type and KHK knockout (KHK-KO) mice had similar blood glucose levels following STZ injection (FIG. 10A), but KHK KO mice were protected from polyuria (FIG. 10B), glycosuria (FIG. 10C), phosphaturia (FIG. 10D), and tubular injury, as noted by urinary NGAL excretion (FIG. 10E) and urinary albumin excretion (FIG. 10F). The renal injury in the wild type mice was also associated with an increase in serum creatinine, documenting impaired renal function that was blocked in the KHK-KO mice (FIG. 10G). Histologic injury, consisting of loss of brush border, vacuolization, tubular atrophy and proliferation, was also present in the diabetic wild type mice (FIG. 10H) but absent in the KHK KO mice (FIG. 1).

The studies in these examples document for the first time that blocking KHK can prevent the tubular injury induced by diabetes. Since tubular injury is critical not only for acute diabetic disease, but also for the development of chronic diabetic renal disease[24], the blockade of KHK will have significant benefits in preventing both acute and chronic diabetic nephropathy. In addition, since our later studies (see below) show that it is the KHK-C isoform that is primarily responsible for causing the inflammatory response, our studies suggest that either (a), a general KHK inhibitor (against both isoforms KHK-A or KHK-C); or (b) a KHK-C-specific inhibitor as are fully described herein should be protective for acute and chronic diabetic nephropathy.

Critically also, the present inventors have also found that the renal KHK pathway likely has a major role in all forms of acute kidney injury. This is because AR and SDH can be upregulated by a variety of stimuli, and since there is normally large amounts of glucose being absorbed in the proximal tubule, such an upregulation would be hypothesized to activate KHK and cause local renal injury. We have specific evidence for this in two different types of acute kidney injury (AKI).

Figures 11A, 11B, 11C:
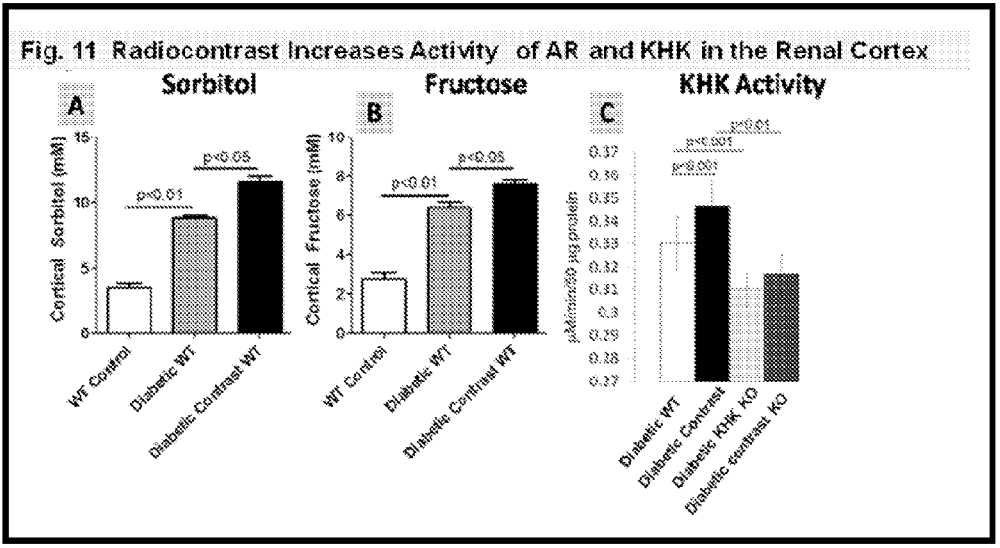
FIGS. 11A-11C show the injection of contrast resulted in a significant increase in renal cortical levels of sorbitol (FIG. 11A), fructose (FIG. 11B), and KHK activity (FIG. 11C) in the diabetic wild type (WT) mouse compared to the control diabetic WT mouse not administered contrast, documenting that contrast induces an acute increase in aldose reductase (AR) and fructokinase (KHK) activity in the renal cortex.

The first example is radiocontrast nephrotoxicity. It had been known that both hyperosmolar and iso-osmolar radiocontrast can induce AKI in patients, but the reason remained unknown. Hyperosmolar contrast is considered more nephrotoxic than isoosmolar contrast, but both can cause AKI, especially in subjects with diabetes. We performed a classical model of contrast-induced AKI in diabetic wild type (WT) and KHK KO mice using isoosmolar contrast (Isovue) (FIGS. 11A-11C).[24] As shown in FIGS. 11A-11C, the injection of contrast resulted in a significant increase in renal cortical levels of sorbitol (FIG. 11A), fructose (FIG. 11B), and KHK activity (FIG. 11C), documenting that contrast (regardless of osmolarity) induces an acute increase in KHK activity in the proximal tubule.

Figures 12A, 12B, 12C, 12D, 12E:
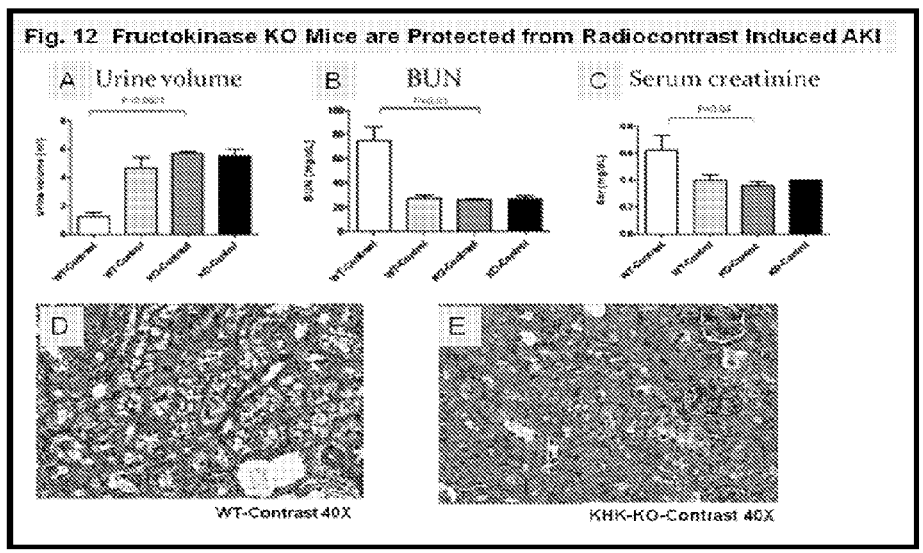
FIGS. 12A-12E show that tubular injury was marked in the diabetic WT mice receiving radiocontrast, but was completely blocked in the diabetic KHK KO mice receiving contrast as it relates to oliguria (Fig A), serum BUN and creatinine levels (Figs B and C), and histologic injury (Figs D and E).

It was also shown that proximal tubular injury was marked in the WT mice receiving radiocontrast, but was completely blocked in the KHK KO mice (FIGS. 12A-12E). First, whereas WT mice developed marked oliguria following contrast injection, this was prevented in the KHK KO mice (FIG. 12A). More importantly, diabetic WT mice receiving contrast showed marked elevations in both BUN and creatinine (FIGS. 12C and 12D) that was prevented in KHK KO mice. Severe proximal tubular injury as noted by loss of brush border and local inflammation was also present in the WT mice receiving contrast (FIG. D), but was absent in similarly treated KHK KO mice (FIG. 12E). These studies demonstrate a novel role for blocking KHK as a means to prevent radiocontrast associated AKI.

Figure 13:
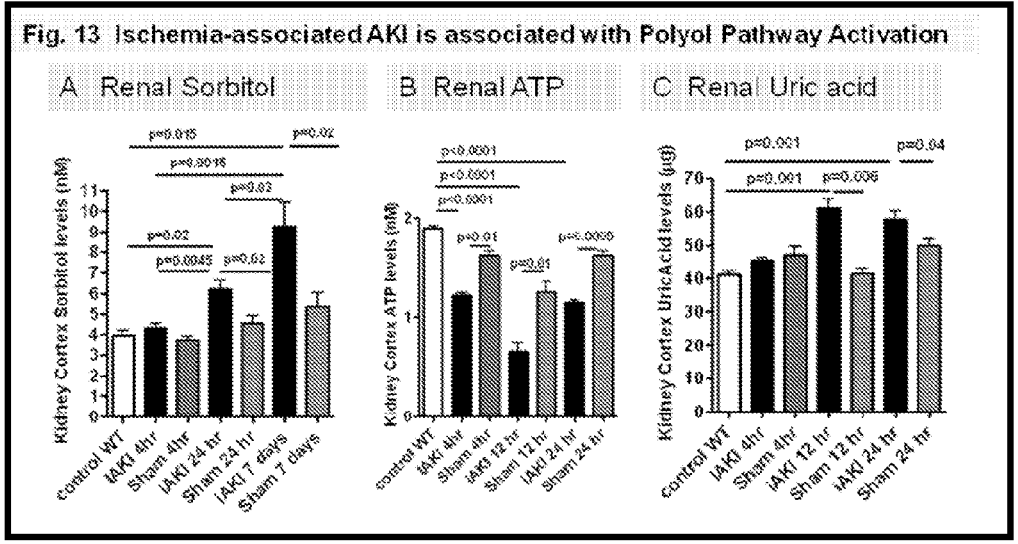
FIG. 13 shows ischemia reperfusion in mice in which increased renal cortical activity of aldose reductase (AR) is apparent, as noted by increased renal sorbitol (FIG. 1) as well as increased activity of fructokinase, as noted by reduced ATP levels (Figure B) and increased renal cortical uric acid levels (Figure C).

A second example is AKI following ischemia-reperfusion, such as following cardiovascular surgery. A role for endogenous fructose or KHK has never been considered as a target for prevention or treatment of AKI from this condition. However, ischemia is known to regulate AR, and we found that ischemia reperfusion in mice (IAKI) is associated with increased renal cortical levels of sorbitol consistent with AR activation (FIG. 13A) and low ATP and high intrarenal uric acid levels consistent with KHK activation (FIGS B and C). These studies strongly suggest that AKI associated with ischemia reperfusion will also be mediated by KHK.

In addition, other forms of AKI include the AKI associated with IgG therapy in which sorbitol (which is in the solution containing the IgG) is thought to play a role. No one had thought of the role of KHK in this form of AKI, but since sorbitol is a substrate for SDH and will result in fructose production, AKI associated with IgG therapy is likely to be a KHK-dependent form of AKI. Likewise, sepsis also results in ischemia to the kidney and hence the AKI from sepsis is likely KHK dependent. This suggests that blockade of KHK should be helpful in most forms of AKI, both in terms of prevention (such as for specific insults such as from contrast, sorbitol, or following cardiovascular or other surgeries) or for both prevention or treatment where the insult can be prolonged (such as in diabetes, with sepsis, and with recurrent ischemia such as in subjects in the ICU).

In accordance with another aspect of the present invention, the present inventors have found that a KHK-C inhibitor that blocks either both isoforms of KHK (KHK-A or KHK-C), or only blocks KHK-C, will be useful for the prevention of diabetic renal disease. This will include blocking the acute tubular injury and polyuria associated with uncontrolled diabetes, as well as acute renal failure syndromes occurring in diabetes from radiocontrast, sepsis or ischemia, and chronic diabetic kidney disease. Since diabetes markedly increases the risk for these complications independent of whether it is type 1 or type 2 diabetes, the administration of a KHK inhibitor will be useful in treating any subject diagnosed with diabetes mellitus (fasting blood sugar>125 mg/dl).

In accordance with another aspect of the present invention, a KHK-C inhibitor that blocks either both isoforms, or only blocks isoform C will be useful for treating and preventing acute tubular injury and polyuria associated with uncontrolled diabetes, as well as acute renal failure syndromes occurring in diabetes from radiocontrast, sepsis or ischemia, and for the treatment of chronic diabetic kidney disease, defined either as incipient diabetic nephropathy (presence of microalbuminuria, or urinary albumin from 30 to 300 mg/d) or frank diabetic nephropathy (urinary albumin excretion>300 mg/d).

In accordance with another aspect of the present invention, a KHK-C inhibitor that blocks either both isoforms, or only blocks isoform C, will be useful for the treating or preventing of acute kidney injury from radiocontrast, sepsis, or ischemia in the absence of diabetes. Specifically, the administration of a KHK inhibitor may be provided to the subject prior to the administration of radiocontrast, or prior to extensive cardiovascular surgery, or in a subject suspected of developing sepsis. Subjects particularly at high risk include those with baseline reduction in renal function (defined as estimated GFR <60/ml/min or stage 3 chronic kidney disease or higher), subjects with marked proteinuria (>300 mg/d), subjects with, a prior history of acute kidney injury, subjects with elevated uric acid (>6 mg/dl), subjects with diabetes, or subjects with poor hepatic or cardiac function.

In accordance with one aspect of the present invention, given the pathway shown in FIG. 8, there is provided a method for reducing ATP depletion, MCP-1 production, and/or intrarenal uric acid production in a subject, the method comprising inhibiting KHK-C activity in the subject. In one embodiment, the inhibiting is done by administering a KHK-C inhibitor to the subject.

In accordance with another aspect of the present invention, there is provided a method for treating a diabetic renal complication in a subject, the method comprising administering a KHK-C inhibitor to the subject. The diabetic renal complication may include one or more of acute polyuria, tubular dysfunction, and acute renal injury. In one embodiment, the KHK-C inhibits KHK-C, but does not inhibit KHK-A.

In accordance with another aspect of the present invention, there is provided a method for inhibiting KHK-C activity in a subject comprising administering to the subject an effective amount of a KHK-C inhibitor.

In accordance with another aspect of the present invention, there is provided a method for treating or preventing renal tubular injury in a subject. The method comprises administering a KHK-C inhibitor to the subject.

In accordance with another aspect of the present invention, there is provided a method of improving kidney tubular function in a subject in need. The method comprises inhibiting KHK-C, or both KHK-A or KHK-C in the subject, wherein the subject in need is exhibiting polyuria or volume depletion or both associated with diabetes.

In accordance with another aspect of the present invention, there is provided a method of treating diabetic polyuria in a subject. The method comprises inhibiting KHK-C or both KHK-A and KHK-C in said subject, such as by administering a KHK-C inhibitor.

In accordance with another aspect of the present invention, there is provided a method of treating diabetic nephropathy in a subject. The method comprises inhibiting KHK-C or both KHK-A and KHK-C in said subject, such as by administering a KHK-inhibitor to the subject.

In accordance with another aspect of the present of invention, there is provided a method for treating or preventing contrast acute kidney injury (AKI) associated with administration of a radiocontrast agent in a subject comprising administering a KHK-C inhibitor to the subject.

In accordance with another aspect of the present invention, there is provided a composition for reducing ATP depletion, MCP-1 production, and/or intrarenal uric acid production comprising a KHK-C inhibitor.

In accordance with another aspect of the present invention, there is provided a composition for treating or preventing contrast acute kidney injury (AKI) associated with administration of a radiocontrast agent in a subject comprising a KHK-C inhibitor. Also, the composition can be administered proximate to cardiovascular surgery. In a specific embodiment, the composition is administered 2 weeks, 1 week, 3 days, 24 hours prior to the surgery and/or after surgery.

In accordance with another aspect of the present invention, there is provided a composition for treating or preventing renal tubular injury comprising a KHK-C inhibitor.

In accordance with another aspect of the present invention, there is provided a composition for a renal complication characterized by an increased presence or activity of KHK-C comprising a KHK-C inhibitor.

In accordance with another aspect of the present invention, there is provided a composition for treating or preventing a renal complication characterized by an increased presence or activity of KHK-C comprising a KHK-C inhibitor.

In one embodiment, the disease characterized by an increased presence or activity of KHK-C is acute kidney injury (AKI) associated with administration of a contrast agent, AKI associated with IgG therapy, or AKI following ischemia-reperfusion, for example. While not wishing to be bound by theory, it is believed that the radiocontrast administration, for example, upregulates aldose reductaase (AR) activity, and thus downstream sorbitol dehydrogenase (SDH) and KHK-C production (See FIG. 1), due to the hyperosmolarity of the contrast agent. The high amount of glucose that is normally absorbed in the proximal tubule then acts to generate fructose and its toxic endproducts, e.g., uric acid, oxidants, and chemokines, e.g., MCP-1.

AKI may be defined by according to known diagnostic measures in the art. In one embodiment, AKI is characterized by a rapid time course (less than 48 hours), wherein there exist a reduction of kidney function as characterized by a rise in serum creatinine, such as: an absolute increase in serum creatinine of ≥0.3 mg/dl (≥26.4 μmol/l); a percentage increase in serum creatinine of ≥50%; and/or a reduction in urine output, defined as <0.5 ml/kg/hr for more than 6 hours.

In another embodiment, the disease characterized by an increased presence or activity of KHK-C is a renal complication, such as renal tubular injury or renal tubular toxicity. Renal tubular injury may be characterized by the presence of degenerative lesions of the renal tubules, such as acute tubular dilation, vacuolation, and necrosis. Renal tubular injury may result from the exposure of the tubules to oxidative stress and inflammatory mediators, such as MCP-1. Polyuria is a condition usually defined as excessive or abnormally large production and/or passage of urine (at least 2.5 or 3 L over 24 hours in adults). When both polyuria and tubular toxicity are present, they may be collectively referred to as acute polyuria/tubular toxicity. In one embodiment, the compositions and methods are utilized in milder complications from renal injury, such as polyuria mentioned above and Fanconi-like syndrome.

In specific embodiments, therapeutic agents are used to treat a patient suffering from symptoms of kidney disease (KD) stages:
  KD stage 1: normal or increased glomerular filtration rate (GFR); some evidence of kidney damage reflected by microalbuminuria/proteinuria, hematuria or histologic changes.

KD stage 2: mild decrease in GFR (defined as 89-60 ml/min/1.73 m2) as defined by MDRD GFR.

KD stage 3 as moderate decrease in GFR (59-30 ml/min/1.73 m2) as defined by MDRD GFR.

KD stage 4 as severe decrease in GFR (29-15 ml·min/1.73 m2)

Chapter 4: General

The following information applies to any of the compositions, methods, or the like described above in 1-3 with respect to sugar craving, obesity and renal disease, for example.

In accordance with one aspect of the present invention, there is provided a method for reducing ATP depletion, MCP-1 production, and/or intrarenal uric acid production in a subject. The method comprises administering a KHK-C inhibitor to the subject.

In accordance with another aspect of the present invention, there is provided a method for inhibiting KHK-C activity in a subject comprising administering a KHK-C inhibitor to the subject.

In accordance with another aspect of the present invention, there is provided a composition for treating or preventing a complication characterized by an increased presence or activity of KHK-C comprising a KHK-C inhibitor.

In one embodiment, the KHK inhibitor inhibits KHK-C, but does not inhibit KHK-A. By not inhibiting KHK-A, it is meant that the inhibitor is specifically targeted to inhibit the activity of KHK-C and that this results in the activity or expression of KHK-C being inhibited to a greater extent than the activity or expression of KHK-A. While not wishing to be bound by theory, it is believed that KHK-A at least metabolizes fructose less rapidly than KHK-C as indicated by its higher Km value. Further, while not wishing to be bound by theory, it is believed that due to its higher Km and its more ubiquitous distribution, KHK-A may not induce the same severity of ATP depletion or intracellular uric acid generation with fructose as seen with KHK-C. Nevertheless, in certain embodiments, the KHK-C inhibitor may inhibit KHK-C activity, as well as KHK-A activity.

The KHK-C inhibitor may include one or more of a ribozyme, an interfering molecule, a peptide, a small molecule, or an antibody targeted to KHK-C. In a particular embodiment, the KHK-C inhibitor comprises an interfering molecule that can participate in changes in gene expression of KHK-C, such as the silencing of expression of the KHK-C and optionally KHK-A. Without limitation, the interfering molecule may comprise a phosphothioate morpholino oligomer (PMO), miRNA, siRNA, shRNA, any other antisense sequence, or any combination thereof.

The methods and compositions as described herein may be utilized in the treatment of any disease characterized by an increased presence or activity of KHK-C. KHK-C is believed to be expressed in three major tissues: the liver, the intestines, and the S3 segment of the proximal tubule of the kidney. In one embodiment, the compositions and methods inhibit the activity of KHK-C in the S3 segment of the proximate tubule. Further, it is noted that the compositions and methods described herein are not limited to their use on diabetic subjects. In one embodiment, the subject may be non-diabetic, such as a non-diabetic individual undergoing radiocontrast administration, or who is to undergo cardiovascular surgery, or who is septic. In another embodiment, the subject is, in fact, diabetic. Diabetic subjects appear to be even more susceptible to adverse activity by KHK-C due to increased amounts of endogenously produced-fructose in the subject from glucose.

KHK can be inhibited by a number of means as set forth further below, including silencing via miRNA, shRNA, siRNA, or a PMO directed to a portion of the sequence described at the genbank accession numbers provided below. See U.S. Patent Publication 20060110440 for background on siRNA silencing, the entirety of which is hereby incorporated by reference. As discussed above, agents can be developed inhibit KHK-C, or both KHK-A and KHK-C to achieve a beneficial effect on obesity, sugar cravings and evidence of glucose-induced tubular dysfunction of the kidney.

It is noted that the compositions and methods disclosed herein may be administered to any subject as defined herein. In one embodiment, the subject is human. In another embodiment, the subject is a pet, e.g., cat, dog, or the like, and in a particular embodiment, is an overweight pet or animal. It is further noted that a corresponding composition, e.g., a pharmaceutical composition, may be provided for use in any method described herein.

Screening Methods

The invention provides assays for screening test compounds which bind to or modulate the activity of a KHK polypeptide or bind to and inhibit or affect expression of a KHK polynucleotide. A test compound preferably binds to a KHK polypeptide. More preferably, a test compound decreases or increases KHK activity by at least about 10, preferably about 50, more preferably about 75, 90, or 100% relative to the absence of the test compound.

In accordance with one aspect of the present invention, there is provided a method of screening for compounds capable of differentially inhibiting KHK-C relative to KHK-A. The method comprises contacting at least one KHK inhibitor test compound with a KHK-C polypeptide. In addition, the method comprises detecting binding of said at least one KHK inhibitor test compound to said KHK-C polypeptide, wherein a test compound which binds to said KHK-C polypeptide is identified as potential KHK inhibitor agent.

In accordance with another aspect of the present invention, there is provided a method of screening for compounds capable of inhibiting KHK-C. The method comprises i) determining the activity of a KHK-C polypeptide without contact with a test compound; and ii) determining the activity of said KHK-C polypeptide upon contact with the test compound, wherein a test compound that modulates activity of said KHK-C polypeptide is identified as potential KHK inhibitor agent.

Test Compounds

Test compounds relate to agents that potentially have therapeutic activity, i.e., bind to or modulate the activity of a KHK polypeptide or bind to or affect expression of a KHK polynucleotide. Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl.

Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and inhibit KHK polypeptides or polynucleotides or to affect KHK activity or KHK gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format. Alternatively, "free format assays," or assays that have no physical barrier between samples, can be used.

1.3. Binding Assays

For binding assays, the test compound is preferably, but not necessarily, a small molecule which binds to and occupies, for example, the active site of the KHK polypeptide, such that normal biological activity is prevented. Examples of such small molecules include, but are not limited to, small peptides or peptide-like molecules.

In binding assays, either the test compound or the KHK polypeptide can comprise a detectable label, such as a fluorescent, radioisotopic, chemiluminescent, or enzymatic label, such as horseradish peroxidase, alkaline phosphatase, or luciferase. Detection of a test compound which is bound to the KHK polypeptide can then be accomplished, for example, by direct counting of radioemission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a KHK polypeptide can be determined without labeling either of the interactants. A microphysiometer can be used to detect binding of a test compound with a KHK polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and a KHK polypeptide (McConnell et al., Science 257, 19061912, 1992).

In another alternative example, determining the ability of a test compound to bind to a KHK polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a KHK polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the KHK polypeptide and modulate its activity.

In many screening embodiments, it may be desirable to immobilize either the KHK polypeptide (or polynucleotide) or the test compound to facilitate separation of bound from unbound forms of one or both of the interactants, as well as to accommodate automation of the assay. Thus, either the KHK polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the KHK polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a KHK polypeptide (or polynucleotide) can be accomplished in any vessel suitable for containing the reactants. Examples of such vessels include microtiter plates, test tubes, and microcentrifuge tubes.

In a specific embodiment, the KHK polypeptide may be a fusion protein comprising a domain that allows the KHK polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed KHK polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a KHK polypeptide (or polynucleotide) or a test compound can be immobilized utilizing conjugation of biotin and streptavidin. Biotinylated KHK polypeptides (or polynucleotides) or test compounds can be prepared from biotinNHS(Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a KHK polypeptide, polynucleotide, or a test compound, but which do not interfere with a desired binding site, such as the active site of the KHK polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the KHK polypeptide or test compound, enzyme-linked assays which rely on detecting an activity of the KHK polypeptide, and SDS gel electrophoresis under non-reducing conditions.

Screening for test compounds which bind to a KHK polypeptide or polynucleotide also can be carried out in an intact cell. Any cell which comprises a KHK polypeptide or polynucleotide can be used in a cell-based assay system. A KHK polynucleotide can be naturally occurring in the cell or can be introduced using techniques such as those described above. Binding of the test compound to a KHK polypeptide or polynucleotide is determined as described above.

1.4. Enzyme Assays

Test compounds can be tested for the ability to increase or decrease the KHK activity of a KHK polypeptide. KHK activity can be measured such as by that described in the Examples. Enzyme assays can be carried out after contacting either a purified KHK polypeptide, a cell membrane preparation, or an intact cell with a test compound. A test compound which decreases TGS activity of a KHK polypeptide by at least about 10, preferably about 50, more preferably about 75, 90, or 100% is identified as a potential therapeutic agent for decreasing KHK activity. A test compound which increases TGS KHK polypeptide by at least about 10, preferably about 50, more preferably about 75, 90, or 100% is identified as a potential therapeutic agent for increasing TGS activity.

1.5. Gene Expression

In another embodiment, test compounds which increase or decrease KHK gene expression are identified. A KHK polynucleotide is contacted with a test compound, and the expression of an RNA or polypeptide product of the KHK polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of KHK mRNA or polypeptide expression in the cells can be determined by methods well known in the art for detecting mRNA or polypeptide. Either qualitative or quantitative methods can be used. The presence of polypeptide products of a KHK polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a KHK polypeptide.

Such screening can be carried out either in a cell-free assay system or in an intact cell. Any cell which expresses a KHK polynucleotide can be used in a cell-based assay system. The KHK polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also pertains to compositions, e.g., pharmaceutical compositions, comprising one or more therapeutic agents that inhibit KHK-C, or both KHK-A and KHK-C, or stimulate KHK-A but not KHK-C. In one embodiment, the therapeutic agents inhibit KHK-C, but not KHK-A as KHK-C. Therapeutic agents include those that are identified by screening methods that utilize KHK polypeptides and/or polynucleotides. Therapeutic agent(s) can be administered to a patient to achieve a therapeutic effect, i.e. useful in modulating KHK activity and in turn, treating and/or preventing obesity, sugar cravings, and/or tubular function. Compositions of the invention can comprise, for example, therapeutic agents identified by a screening method embodiment described herein, which are identified by their ability to bind to or affect activity of KHK polypeptides, or bind to and/or affect expression of KHK polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these compositions can contain suitable pharmaceutically acceptable carriers comprising excipients and auxiliaries which facilitate processing of the active compounds into preparations which can be used pharmaceutically. Compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Accordingly, some examples of an agent having therapeutic activity as described herein, include but are not limited to a modulating agent, an antisense nucleic acid molecule, small molecule KHK inhibitors, peptide inhibitors, a specific antibody, ribozyme, interfering molecules, or a KHK polypeptide binding molecule targeted to KHK-C, or both KHK-C and KHK-A. In one embodiment, the agent comprises an interfering molecule and the interfering molecule comprises a phosphothioate morpholino oligomer (PMO), miRNA, methylated miRNA, treated-miRNA, siRNA, shRNA, antisense RNA, and any combination thereof.

Each of the compositions and methods described herein may include an effective amount of the KHK-C inhibitor. In one embodiment, the KHK-C inhibitor is combined with one or more conjunctive therapeutic agents to bring about a desired effect in the subject. This effect may be realized by an effective amount of the KHK-C inhibitor, an effective amount of the conjunctive agent, or an effective amount of the combination of the KHK-C and the one or more conjunctive therapeutic agents. It is understood that the administration of the KHK-C inhibitor with one or more therapeutic agents may advantageously increase an efficacy of the KHK-C inhibitor, the conjunctive agent, or both.

In certain embodiments, inhibiting KHK involves down-regulation of gene expression, translation or activity of KHK genes. There are two isoforms of KHK relevant to therapeutic activity discussed below, as well as for screening and production of therapeutic agents: KHK-C (predominant form of KHK, Gen Bank Accession #NM_006488

SEQ. ID. Nos 1 & 2 and KHK-A (Gen Bank Accession#NM_000221 (http://www.ncbi.nlm.nih.gov/entrez/viewerfcgi?db=nucleotide&val=4557692) SEQ. ID. Nos. 3 & 4.

The methods and compositions described herein may be directed at inhibiting expression of inhibiting the gene expression, translation or activity of any one or more of these KHK genes. In a particular embodiment, the methods and compositions described herein are directed at inhibiting the gene expression, translation or activity of KHK-C.

Agents can be used in an animal model to determine the efficacy, toxicity, or side effects of treatment with such an agent. In addition, compositions may include a conjunctive agent in addition to the therapeutic agents of the present invention. A comprehensive discussion of many different agents that can be used in combination with a therapeutic agent comprising a KHK inhibitor is described in U.S. Patent Pub. 20080255101, the entirety of which is incorporated by reference herein. According to specific embodiments, small molecule KHK inhibitors include, but are not limited to, 1-deoxy-fructose or 5-thio-d-fructose. See Raushel and Cleland, Biochemistry, 16:2169-2175 (1977).

Exemplary compounds include for use with the therapeutic agent(s) or composition comprising a KHK-C inhibitor as described herein may be selected from the group consisting of angiotensin-converting enzyme (ACE) inhibitors, aldosterone antagonists, amphetamines, amphetamine-like agents, Angiotensin II receptor antagonists, anti-oxidants, aldose reductase inhibitors, biguanides, sorbitol dehydrogenase inhibitors, thiazolidinediones (glitazones), thiazide and thiazide-like diuretics, triglyceride synthesis inhibitors, uric acid lowering drugs, e.g., xanthine oxidase inhibitors, and combinations thereof.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about 106 cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes conventionally used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which modulates KHK activity compared to that which occurs in the absence of the therapeutically effective dose.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration; drug combination(s), reaction sensitivities, and tolerance/response to therapy. Long-acting compositions can be administered every 3 to 4 days, every week, or once every two weeks depending on the half-life and clearance rate of the particular formulation.

Normal dosage amounts can vary from 0.1 to 100,000 micrograms, up to a total dose of about 0.1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, a therapeutic agent reduces expression of a KHK gene or the activity of a KHK polypeptide by at least about 10, preferably about 50, more preferably about 75, 90, or 100% relative to the absence of the reagent. The effectiveness of the mechanism chosen to decrease the level of expression of a KHK gene or the activity of a KHK polypeptide can be assessed such as by hybridization of nucleotide probes to KHK-specific mRNA, quantitative RT-PCR, immunologic detection of a KHK polypeptide, or measurement of KHK activity.

2.2 Conjunctive Therapeutic Agents

In any of the embodiments described above, any of the compositions of the invention can be co-administered with other appropriate therapeutic agents (conjunctive agent or conjunctive therapeutic agent) for the treatment or prevention of a target disease. Selection of the appropriate conjunctive agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods and compositions comprising a KHK-C inhibitor described herein can be co-administered with another conjunctive agent to a subject in need of such therapy.

Exemplary conjunctive agents that may be formulated and/or administered with any form of a KHK-C inhibitor as described herein include, but are not limited to, angiotensin-converting enzyme (ACE) inhibitors, aldosterone antagonists, amphetamines, amphetamine-like agents, Angiotensin II receptor antagonists, anti-oxidants, aldose reductase inhibitors, biguanides, sorbitol dehydrogenase inhibitors, thiazolidinediones (glitazones), thiazide and thiazide-like diuretics, triglyceride synthesis inhibitors, uric acid lowering agents, e.g., xanthine oxidase inhibitors, and combinations thereof.

Exemplary ACE inhibitors include, but are not limited to, Benazepril (Lotensin), Captopril, Enalapril (Vasotec), Fosinopril, Lisinopril (Prinivil, Zestril), Moexipril (Univasc), Perindopril (Aceon), Quinapril (Accupril), Ramipril (Altace), Trandolapril (Mavik), and combinations thereof.

Exemplary aldosterone antagonists include, but are not limited to, Spironolactone, Eplerenone, Canrenone (canrenoate potassium), Prorenone (prorenoate potassium), Mexrenone (mexrenoate potassium), and combinations thereof.

Exemplary amphetamines include, but are not limited to, amphetamine, methamphetamine, methylphenidate, p-methoxyamphetamine, methylenedioxyamphetamine, 2,5-dimethoxy-4-methylamphetamine, 2,4,5-trimethoxyamphetamine, and 3,4-methylenedioxymethamphetamine, N-ethylamphetamine, fenethylline, benzphetamine, and chlorphentermine as well as the amphetamine compounds of Adderall®; actedron; actemin; adipan; akedron; allodene; alpha-methyl-(.+-.)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine; rhinalator, sympamine; simpatedrin; simpatina; sympatedrine; and weckamine. Exemplary amphetamine-like agents include but are not limited to methylphenidate. Exemplary compounds for the treatment of ADD include, but are not limited to, methylphenidate, dextroamphetamine/amphetamine, dextroamphetamine, and atomoxetine (non-stimulant).

Exemplary Angiotensin II receptor antagonists or angiotensin receptor blockers (ARBs) include, but are not limited to losartan, irbesartan, olmesartan, candesartan, valsartan, and combinations thereof.

Exemplary anti-oxidant compounds include but are not limited to L-ascorbic acid or L-ascorbate (vitamin C), menaquinone (vitamin K 2), plastoquinone, phylloquinone (vitamin K 1), retinol (vitamin A), tocopherols (e.g., α, β, γ and δ-tocotrienols, ubiquinol, and ubiquione (Coenzyme Q10)); and cyclic or polycyclic compounds including acetophenones, anthroquinones, benzoquiones, biflavonoids, catechol melanins, chromones, condensed tannins, coumarins, flavonoids (catechins and epicatechins), hydrolyzable tannins, hydroxycinnamic acids, hydroxybenzyl compounds, isoflavonoids, lignans, naphthoquinones, neolignans, phenolic acids, phenols (including bisphenols and other sterically hindered phenols, aminophenols and thiobisphenols), phenylacetic acids, phenylpropenes, stilbenes and xanthones. Additional cyclic or polycyclic antioxidant compounds include apigenin, auresin, aureusidin, Biochanin A, capsaicin, catechin, coniferyl alcohol, coniferyl aldehyde, cyanidin, daidzein, daphnetin, deiphinidin, emodin, epicatechin, eriodicytol, esculetin, ferulic acid, formononetin, gernistein, gingerol, 3-hydroxybenzoic acid, 4-hydroxybenzoic acid, 3-hydroxycoumarin, juglone, kaemferol, lunularic acid, luteolin, malvidin, mangiferin, 4-methylumbelliferone, mycertin, naringenin, pelargonidin, peonidin, petunidin, phloretin, p-hydroxyacetophenone, (+)-pinoresinol, procyanidin B-2, quercetin, resveratol, resorcinol, rosmaric acid, salicylic acid, scopolein, sinapic acid, sinapoyl-(S)-maleate, sinapyl aldehyde, syrginyl alcohol, telligrandin umbelliferone and vanillin. Antioxidants may also be obtained from plant extracts, e.g., from blackberries, blueberries, black carrots, chokecherries, cranberries, black currants, elderberries, red grapes and their juice, hibiscus, oregano, purple sweet potato, red wine, rosemary, strawberries, tea (e.g., black, green or white tea), and from various plant ingredients as ellagic acid.

Exemplary aldose reductase inhibitors include, but are not limited to, epalrestat, ranirestat, fidarestat, sorbinil, and combinations thereof.

Exemplary biguanides include, but are not limited to, metformin, and less rarely used phenformin and buformin, proguanil, and combinations thereof.

Exemplary thiazolidinediones include, but are not limited to, troglitazone, pioglitazone, ciglitazone, rosiglitazone, englitazone, and combinations thereof.

Exemplary sorbitol dehydrogenase inhibitors are disclosed in U.S. Pat. Nos. 6,894,047, 6,570,013, 6,294,538, and US Published Patent Application No. 20050020578, the entirety of which are incorporated by reference herein.

Exemplary thiazide and thiazide-like diuretics include, but are not limited to, benzothiadiazine derivatives, chlortalidone, metolazone, and combinations thereof.

Exemplary triglyceride synthesis inhibitors include, but are not limited to, diglyceride acyltransferase 1 (DGAT-1) inhibitors.

Exemplary uric acid lowering agents include, but are not limited to, xanthine oxidase inhibitors, such as allopurinol, oxypurinol, tisopurine, febuxostat, inositols (e.g., phytic acid and myo-inositol), and combinations thereof.

It is appreciated that suitable conjuvant therapeutic agents for use in the present invention may also comprise any combinations, prodrugs, pharmaceutically acceptable salts, analogs, and derivatives of the above compounds.)

In one embodiment, the KHK-C inhibitor may be administered to the subject along with one or more other therapeutic agents that are active in acute and chronic kidney disease. Exemplary conjuvant therapeutic agents for this use include but are not limited to angiotensin-converting enzyme (ACE) inhibitors, aldosterone antagonists, Angiotensin II receptor antagonists, anti-oxidants, aldose reductase inhibitors, biguanides, sorbitol dehydrogenase inhibitors, thiazolidinediones (glitazones), xanthine oxidase inhibitors, and/or any other agent used to treat acute or chronic kidney disease.

In another embodiment, the KHK inhibitors may be administered along with other agents in the treatment of metabolic syndrome, obesity, sugar addiction, sugar craving, and attention deficit disorder. Exemplary conjuvant therapeutic agents for this purpose include Exemplary conjunctive agents that may be formulated and/or administered with any form of a KHK-C inhibitor as described herein include, but are not limited to, angiotensin-converting enzyme (ACE) inhibitors, aldosterone antagonists, amphetamines, amphetamine-like agents, Angiotensin II receptor antagonists, anti-oxidants, aldose reductase inhibitors, sorbitol dehydrogenase inhibitors, thiazide and thiazide-like diuretics, triglyceride synthesis inhibitors, and/or any other agent used to treat metabolic syndrome, obesity, sugar addiction, sugar craving, and/or attention deficit disorders.

It is appreciated by one skilled in the art that when any one or more the KHK inhibitors described herein are combined with an conjuvant therapeutic agent, the KHK inhibitor(s) may critically allow for increased efficacy of the conjuvant therapeutic agent or allow for reduction of the dose of the other therapeutic agent that may have a dose-related toxicity associated therewith.

The mode of administration for a conjunctive formulation in accordance with the present invention is not particularly limited, provided that the KHK-C inhibitor and the conjunctive agent are combined upon administration. Such an administration mode may, for example, be (1) an administration of a single formulation obtained by formulating a KHK-C inhibitor and the conjunctive agent simultaneously; (2) a simultaneous administration via an identical route of the two agents obtained by formulating a KHK-C inhibitor and a conjunctive agent separately; (3) a sequential and intermittent administration via an identical route of the two agents obtained by formulating a KHK-C inhibitor and a conjunctive agent separately; (4) a simultaneous administration via different routes of two formulations obtained by formulating a KHK-C inhibitor and a conjunctive agent separately; and/or (5) a sequential and intermittent administration via different routes of two formulations obtained by formulating a KHK-C inhibitor and a conjunctive agent separately (for example, a KHK-C or its composition followed by a conjunctive agent or its composition, or inverse order) and the like.

The dose of a conjunctive formulation may vary depending on the formulation of the KHK-C inhibitor and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When a KHK-C inhibitor and a conjunctive agent are administered to a subject, the agents may be administered at the same time, but it is also possible that the conjunctive agent is first administered and then the KHK-C inhibitor is administered, or that the KHK-C is first administered and then the conjunctive agent is administered. When such an intermittent administration is employed, the time interval may vary depending on the active ingredient administered, the dosage form and the administration mode, and for example, when the conjunctive agent is first administered, the KHK-inhibitor may be administered within 1 minute to 3 days, preferably 10 minutes to 1 day, more preferably 15 minutes to 1 hour after the administration of the conjunctive agent. When the KHK-C inhibitor is first administered, for example, then the conjunctive agent may be administered within 1 minute to 1 day, preferably 10 minutes to 6 hours, more preferably 15 minutes to 1 hour after the administration of the KHK-C inhibitor.

It is understood that when referring to a KHK-C inhibitor and a conjunctive agent, it is meant a KHK-C inhibitor alone, a conjunctive agent alone, as a part of a composition, e.g., composition, which optionally includes one or more pharmaceutical carriers. It is also contemplated that more than one conjunctive agent may be administered to the subject if desired.

Polypeptides

KHK polypeptides according to an aspect of the present invention comprise at least 12, 15, 25, 50, 75, 100, 125, 150, 175, 200, 225, 250 or 265 contiguous amino acids selected from the amino acid sequence shown in SEQ ID NO: 2 and 4, or a biologically active variant thereof, as defined below. A KHK polypeptide of the invention therefore can be a portion of a KHK protein, a full-length KHK protein, or a fusion protein comprising all or a portion of KHK protein.

3.1 Biologically Active Variants

KHK polypeptide variants which are biologically active, i.e., confer an ability to phosphorylate fructose, also are considered KHK polypeptides for purposes of this application. Preferably, naturally or non-naturally occurring KHK polypeptide variants have amino acid sequences which are at least about 55, 60, 65, or 70, preferably about 75, 80, 85, 90, 96, 96, or 98% identical to the amino acid sequence shown in SEQ ID NO: 2 or a fragment thereof. Percent identity between a putative KHK polypeptide variant and an amino acid sequence of SEQ ID NO: 2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a KHK polypeptide can be found using computer programs well known in the art, such as DNASTAR software. Whether an amino acid change results in a biologically active KHK polypeptide can readily be determined by assaying for KHK activity, as described herein, for example.

3.2 Fusion Proteins

In some embodiments of the invention, it is useful to create fusion proteins. By way of example, fusion proteins are useful for generating antibodies against KHK polypeptide amino acid sequences and for use in various assay systems. For example, fusion proteins can be used to identify proteins which interact with portions of a KHK polypeptide. Protein affinity chromatography or library-based assays for protein—protein interactions, such as the yeast two-hybrid or phage display systems, can be used for this purpose. Such methods are well known in the art and also can be used as drug screens.

A KHK polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NO: 2 or of a biologically active variant, such as those described above. The first polypeptide segment also can comprise full-length KHK protein.

The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the KHK polypeptide-encoding sequence and the heterologous protein sequence, so that the KHK polypeptide can be cleaved and purified away from the heterologous moiety.

Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Polynucleotides

A KHK polynucleotide can be single- or double-stranded and comprises a coding sequence or the complement of a coding sequence for a KHK polypeptide. A coding sequence for KHK polypeptide of SEQ ID NO: 2 or 4 is shown in SEQ ID NO: 1 or 3, respectively.

Degenerate nucleotide sequences encoding KHK polypeptides, as well as homologous nucleotide sequences which are at least about 50, 55, 60, 65, 60, preferably about 75, 90, 96, or 98% identical to the nucleotide sequence shown in SEQ ID NO: 1 also are KHK-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of KHK polynucleotides which encode biologically active KHK polypeptides also are KHK polynucleotides.

4.1 Identification of Polynucleotide Variants and Homologs

Variants and homologs of the KHK polynucleotides described above also are KHK polynucleotides. Typically, homologous KHK polynucleotide sequences can be identified by hybridization of candidate polynucleotides to known KHK polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the KHK polynucleotides disclosed herein also can be identified by making suitable probed or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of KHK polynucleotides or polynucleotides of other species can therefore be identified by hybridizing a putative homologous KHK polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to KHK polynucleotides or their complements following stringent hybridization and/or wash conditions also are KHK polynucleotides. Stringent wash conditions are well known and understood in the art and are disclosed, for example, in Sambrook et al., MOLECULAR CLONING: A LABORATORY MANUAL, 2$^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a KHK polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\% G+C) - 0.63(\% \text{ formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring KHK polynucleotide can be, isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated KHK polynucleotides. For example, restriction enzymes and probes can be used to isolate polynucleotide fragments which comprises KHK nucleotide sequences. Isolated polynucleotides are in preparations which are free or at least 70, 80, or 90% free of other molecules.

KHK DNA molecules can be made with standard molecular biology techniques, using KHK mRNA as a template. KHK DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesize KHK polynucleotides. The degeneracy of the genetic code allows alternate nucleotide sequences to be synthesized which will encode a KHK polypeptide having, for example, an amino acid sequence shown in SEQ ID NO: 2 or a biologically active variant thereof.

4.3 Expression of Polynucleotides

To express a KHK polynucleotide, the polynucleotide can be inserted into an expression vector which contains the necessary elements for the transcription and translation of the inserted coding sequence. Methods which are well known to those skilled in the art can be used to construct expression vectors containing sequences encoding KHK polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a KHK enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a KHK polypeptide, vectors based on SV40 or EBV can be used with an appropriate selectable marker.

Host Cells

According to certain embodiments of the subject invention, a KHK polynucleotide will need to be inserted into a host cell, for expression, processing and/or screening. A host cell strain can be chosen for its ability to modulate the expression of the inserted sequences or to process the expressed KHK polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express KHK polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced KHK sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a KHK polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a KHK polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

5.2 Expression and Purification of Polypeptides

Host cells transformed with nucleotide sequences encoding KHK polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode KHK polypeptides can be designed to contain signal sequences which direct secretion of soluble KHK polypeptides through a prokaryotic or eukaryotic cell membrane or which direct the membrane insertion of membrane-bound KHK polypeptide.

Antibodies

Antibodies are referenced herein and various aspects of the subject invention utilize antibodies specific to KHK polypeptide(s). As described above, one example of an therapeutic agent may pertain to an antibody. Any type of antibody known in the art can be generated to bind specifically to an epitope of a KHK polypeptide. "Antibody" as used herein includes intact immunoglobulin molecules, as well as fragments thereof, such as Fab, F(ab')$_2$, and Fv, which are capable of binding an epitope of a KHK polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a KHK polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Ribozymes

Ribozymes may be one category of compounds useful as therapeutic agents for modulating KHK activity. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a KHK polynucleotide to generate ribozymes which will specifically bind to mRNA transcribed from the KHK polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a KHK RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate KHK RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease KHK expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, the entirety of which is incorporated by reference, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

Interfering Molecules

KHK can be inhibited by a number of means including silencing via miRNA, shRNA, or siRNA, for example, directed to a portion of the sequence described at the genbank accession numbers provided above. siRNA molecules can be prepared against a portion of SEQ. ID. Nos 1 and 3 according to the techniques provided in U.S Patent Publication 20060110440 and used as therapeutic compounds. shRNA constructs are typically made from one of three possible methods; (i) annealed complementary oligonucleotides, (ii) promoter based PCR or (iii) primer extension. See Design and cloning strategies for constructing shRNA expression vectors, Glen J McIntyre, Gregory C FanningBMC Biotechnology 2006, 6:1 (5 Jan. 2006).

For background information on the preparation of miRNA molecules, see e.g. U.S. patent applications 20110020816, 2007/0099196; 2007/0099193; 2007/0009915; 2006/0130176; 2005/0277139; 2005/0075492; and 2004/0053411, the disclosures of which are hereby incorporated by reference herein. See also, U.S. Pat. Nos. 7,056,704 and 7,078,196 (preparation of miRNA molecules), incorporated by reference herein. Synthetic miRNAs are described in Vatolin, et al 2006 J Mol Biol 358, 983-6 and Tsuda, et al 2005 Int J Oncol 27, 1299-306, incorporated by reference herein.

It is within the scope of aspects of the present invention to provide agents to silence KHK-C (KHK-C or KHK-A and KHK-C) genes to achieve a therapeutic effect using interfering molecules. In certain embodiments, silencing of human KHK genes should be based on either or both of the sequences of the KHK enzymes mentioned above.

KHK-C Inhibitor Compounds

To document that small molecule compounds can be generated to inhibit KHK-C specifically, the present inventors conducted a virtual screen (computational docking experiment) of the crystal structure of KHK-C and identified compounds from the ZINC database, which had favorable docking scores and demonstrated complementary interactions with the protein based on a follow-up visual inspection of the proposed binding modes. Shown in Table 1 are several compounds that could preferentially inhibit KHK-C over KHK-A. For example, (Z)-3-(methylthio)-1-phenyl-N'-(((4-(trifluoromethoxy)phenyl)carbamoyl)oxy)-1H-pyrazole-4-carboximidamide, [1 in Table 1 below], shows 25.6% inhibition of KHKC at 10 uM and 7.0% inhibition of KHKA at 10 uM. 5-amino-3-(methylthio)-1-phenyl-1H-pyrazole-4-carbonitrile, [2 in Table 1 below], shows 16.8% inhibition of KHKC at 100 uM and 29.4% inhibition of KHKA at 100 uM. 2-(3-(methylthio)-1-phenyl-1H-pyrazol-4-yl)-4-phenylthiazole, [3 in Table 1 below], shows 19.9% inhibition of KHKC at 10 uM.

TABLE 1

| | | | KHKC % inhibition (10 UM) | KHKC % inhibition (100 UM) | KHKA % inhibition (10 UM) | KHKA % inhibition (100 UM) | |
|---|---|---|---|---|---|---|---|
| Structure | Cpd No. | MW | | | | | IUPAC NAME |
| C₁₉H₁₆F₃N₅O₃S | 1 | 451.4 | 25.6 | | 7.0 | | (Z)-3-(methylthio)-1-phenyl-N'-(((4-(trifluoromethoxy)phenyl)carbamoyl)oxy)-1H-pyrazole-4-carboximidamide |
| C₁₁H₁₀N₄S | 2 | 230.3 | 7.8 | 16.8 | 5.7 | 29.4 | 5-amino-3-(methylthio)-1-phenyl-1H-pyrazole-4-carbonitrile |
| C₁₉H₁₅N₃S₂ | 3 | 349.5 | 19.9 | | | | 2-(3-(methylthio)-1-phenyl-1H-pyrazol-4-yl)-4-phenylthiazole |

In accordance with one aspect of the present invention, there is thus provided a method for inhibiting KHK-C activity in a subject. The method comprises administering to the subject an effective amount of a compound selected from the group consisting of:
(Z)-3-(methylthio)-1-phenyl-N'-(((4-(trifluoromethoxy)phenyl)carbamoyl)oxy)-1H-pyrazole-4-carboximidamide;
5-amino-3-(methylthio)-1-phenyl-1H-pyrazole-4-carbonitrile;
2-(3-(methylthio)-1-phenyl-1H-pyrazol-4-yl)-4-phenylthiazole; and
combinations thereof.

In accordance with another aspect of the present invention, there is provided a composition, e.g., a pharmaceutical composition, comprising a KHK-C inhibitor, wherein the KHK-C inhibitor comprises a compound selected from the group consisting of:
(Z)-3-(methylthio)-1-phenyl-N'-(((4-(trifluoromethoxy)phenyl)carbamoyl)oxy)-1H-pyrazole-4-carboximidamide;
5-amino-3-(methylthio)-1-phenyl-1H-pyrazole-4-carbonitrile;
2-(3-(methylthio)-1-phenyl-1H-pyrazol-4-yl)-4-phenylthiazole; and combinations thereof.

The methods and compositions may be utilized to treat or prevent any of the diseases or purposes described herein including, but not limited to renal disease, e.g., acute kidney injury (AKI) associated with administration of a contrast agent, cardiovascular surgery, IgG administration, or sepsis, as well as attention deficit disorder, sugar craving, sugar addiction, obesity, and metabolic syndrome. In addition, one or more of the compounds (1-3) above may be administered to the subject along with one or more conjunctive therapeutic agent as described herein, and the composition may likewise further comprise one or more conjunctive agents as described herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

REFERENCES

1. Johnson R J, Perez-Pozo S E, Sautin Y Y, Manitius J, Sanchez-Lozada L G, Feig D I, et al. Hypothesis: could excessive fructose intake and uric acid cause type 2 diabetes? Endocr Rev. 2009 February; 30(1):96-116.
2. Stanhope K L, Schwarz J M, Keim N L, Griffen S C, Bremer A A, Graham J L, et al. Consuming fructose-sweetened, not glucose-sweetened, beverages increases visceral adiposity and lipids and decreases insulin sensitivity in overweight/obese humans. The Journal of clinical investigation. 2009 May; 119(5):1322-34.
3. Nakagawa T, Hu H, Zharikov S, Tuttle K R, Short R A, Glushakova O, et al. A causal role for uric acid in fructose-induced metabolic syndrome. American journal of physiology. 2006 March; 290(3):F625-31.
4. Perez-Pozo S E, Schold J, Nakagawa T, Sanchez-Lozada L G, Johnson R J, Lillo J L. Excessive fructose intake induces the features of metabolic syndrome in healthy adult men: role of uric acid in the hypertensive response. Int J Obes (Lond). 2009 Dec. 22.
5. Roncal C A, Reungjui S, Sanchez-Lozada L G, Mu W, Sautin Y Y, Nakagawa T, et al. Combination of Captopril and Allopurinol Retards Fructose-Induced Metabolic Syndrome. American journal of nephrology. 2009 Aug. 21; 30(5):399-404.
6. Tran L T, Yuen V G, McNeill J H. The fructose-fed rat: a review on the mechanisms of fructose-induced insulin resistance and hypertension. Mol Cell Biochem. 2009 Jun. 18.
7. Segal M S, Gollub E, Johnson R J. Is the fructose index more relevant with regards to cardiovascular disease than the glycemic index? European journal of nutrition. 2007 October; 46(7):406-17.
8. Cirillo P, Gersch M S, Mu W, Scherer P M, Kim K M, Gesualdo L, et al. Ketohexokinase-dependent metabolism of fructose induces proinflammatory mediators in proximal tubular cells. J Am Soc Nephrol. 2009 March; 20(3): 545-53.
9. Shapiro A, Mu W, Roncal C, Cheng K Y, Johnson R J, Scarpace P J. Fructose-induced leptin resistance exacerbates weight gain in response to subsequent high-fat feeding. American journal of physiology. 2008 November; 295 (5):R1370-5.
10. Teff K L, Elliott S S, Tschop M, Kieffer T J, Rader D, Heiman M, et al. Dietary fructose reduces circulating insulin and leptin, attenuates postprandial suppression of ghrelin, and increases triglycerides in women. The Journal of clinical endocrinology and metabolism. 2004 June; 89(6): 2963-72.
11. Cha S H, Sekine T, Fukushima J I, Kanai Y, Kobayashi Y, Goya T, et al. Identification and characterization of human organic anion transporter 3 expressing predominantly in the kidney. Mol Pharmacol. 2001 May; 59(5):1277-86.
12. Avena N M, Rada P, Hoebel B G. Sugar bingeing in rats. Current protocols in neuroscience/editorial board, Jacqueline N Crawley [et al. 2006 August; Chapter 9:Unit9 23C.
13. de Araujo I E, Oliveira-Maia A J, Sotnikova T D, Gainetdinov R R, Caron M G, Nicolelis M A, et al. Food reward in the absence of taste receptor signaling. Neuron. 2008 Mar. 27; 57(6):930-41.
14. Park S H, Choi H J, Lee J H, Woo C H, Kim J H, Han H J. High glucose inhibits renal proximal tubule cell proliferation and involves PKC, oxidative stress, and TGF-beta 1. Kidney international. 2001 May; 59(5):1695-705.
15. de Araujo I E, Oliveira-Maia A J, Sotnikova T D, Gainetdinov R R, Caron M G, Nicolelis M A, et al. Food reward in the absence of taste receptor signaling. Neuron. 2008 Mar. 27; 57(6):930-41.
16. Shapiro A, Mu W, Roncal C, Cheng K Y, Johnson R J, Scarpace P J. Fructose-induced leptin resistance exacerbates weight gain in response to subsequent high-fat feeding. American journal of physiology. 2008 November; 295 (5):R1370-5.
17. Shapiro A, Tumer N, Gao Y, Cheng K Y, Scarpace P J. Prevention and reversal of diet-induced leptin resistance with a sugar-free diet despite high fat content. The British journal of nutrition. 2011 Mar. 22:1-8.
18. Cirillo P, Gersch M S, Mu W, Scherer P M, Kim K M, Gesualdo L, et al. Ketohexokinase-dependent metabolism of fructose induces proinflammatory mediators in proximal tubular cells. J Am Soc Nephrol. 2009 March; 20(3): 545-53.
19. Gersch M S, Mu W, Cirillo P, Reungjui S, Zhang L, Roncal C, et al. Fructose, but not dextrose, accelerates the progression of chronic kidney disease. American journal of physiology. 2007 October; 293(4):F1256-61.
20. Nakayama T, Kosugi T, Gersch M, Connor T, Sanchez-Lozada L G, Lanaspa M A, et al. Dietary fructose causes tubulointerstitial injury in the normal rat kidney. American journal of physiology. 2010 March; 298(3):F712-20.
21. Diggle C P, Shires M, Leitch D, Brooke D, Carr I M, Markham A F, et al. Ketohexokinase: expression and localization of the principal fructose-metabolizing enzyme. J Histochem Cytochem. 2009 August; 57(8):763-74.
22. Tappy L, Le K A. Metabolic effects of fructose and the worldwide increase in obesity. Physiol Rev. January; 90(1):23-46.
23. Petrash J M. All in the family: aldose reductase and closely related aldo-keto reductases. Cell Mol Life Sci. 2004 April; 61(7-8):737-49.
24. Gilbert R E, Cooper M E. The tubulointerstitium in progressive diabetic kidney disease: more than an aftermath of glomerular injury? Kidney international. 1999 November; 56(5):1627-37.
25. Lee H T, Jan M, Bae S C, Joo J D, Goubaeva F R, Yang J, et al. A1 adenosine receptor knockout mice are protected against acute radiocontrast nephropathy in vivo. American journal of physiology. 2006 June; 290(6):F1367-75.
26. Adelman R C, Ballard F J, Weinhouse S. Purification and properties of rat liver fructokinase. J Biol Chem 1967; 242(14):3360-5.
27. Asipu A, Hayward B E, O'Reilly J, Bonthron D T. Properties of normal and mutant recombinant human ketohexokinases and implications for the pathogenesis of essential fructosuria. Diabetes 2003; 52(9):2426-32.
28. Sanchez J J, Gonzalez N S, Pontis H G. Fructokinase from rat liver. I. Purification and properties. Biochim Biophys Acta 1971; 227(1):67-78.

The teachings of the references, including patents and patent related documents, cited herein are incorporated herein in their entirety to the extent not inconsistent with the teachings herein.

We claim:

1. A method for diminishing, inhibiting or eliminating addiction-related behavior of a human, said method comprising
identifying said human as having a fructose and/or sucrose addiction; and administering to said human an effective amount of a composition comprising a ketohexokinase C (KHK-C) inhibitor to diminish said fructose and/or sucrose addition.

2. A method for treating or protecting against acute kidney injury (AKI) in a subject, the method comprising administering a composition comprising a KHK-C inhibitor; wherein said AKI that is treated or protected against is AKI associated with administration of a contrast agent; AKI associated with cardiovascular surgery; or AKI associated with sepsis.

3. The method of claim 2, wherein the KHK-C inhibitor inhibits KHK-C, but does not inhibit KHK-A.

4. The method of claim 2, wherein the KHK-C inhibitor comprises at least one member of the group consisting of a ribozyme, an interfering molecule, a peptide, a small molecule, or an antibody targeted to KHK-C.

5. The method of claim 4, wherein the KHK-C inhibitor comprises an interfering molecule, and wherein the interfering molecule comprises a member from the group consisting of a phosphorothioate morpholino oligomer (PMO), miRNA, sRNA, methylated sRNA, shRNA, antisense RNA, a dicer-substrate 27-mer duplex, and any combination thereof.

6. The method of claim 2, wherein the administering is done to treat or prevent acute tubular injury.

7. The method of claim 2, further comprising administering to the subject a conjunctive agent, wherein the conjunctive agent comprises a compound selected from the group consisting of angiotensin-converting enzyme (ACE) inhibitors, aldosterone antagonists, amphetamines, amphetamine-like agents, Angiotensin II receptor antagonists, anti-oxidants, aldose reductase inhibitors, biguanides, sorbitol dehydrogenase inhibitors, thiazolidinediones (glitazones), thiazide and thiazide-like diuretics, triglyceride synthesis inhibitors, xanthine oxidase inhibitors, and combinations thereof.

8. A method of treating diabetic nephropathy in a subject, said method comprising administering a KHK-C inhibitor to the subject, wherein the KHK-C inhibitor does not inhibit KHK-A.

* * * * *